Figure 1:
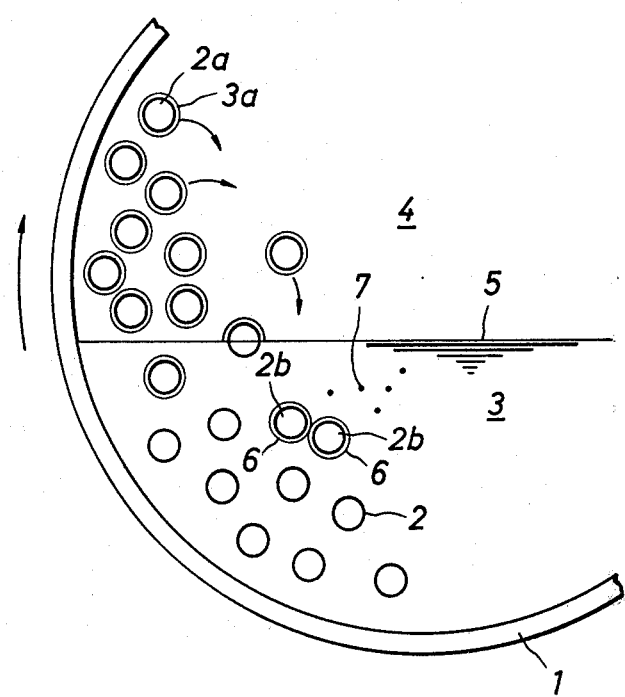

United States Patent [19]

Sugahara et al.

[11] 4,324,768
[45] Apr. 13, 1982

[54] PROCESS FOR PREPARATION OF LEAD COMPOUNDS

[75] Inventors: Yujiro Sugahara, Tokyo; Hiroyuki Naito, Tsuruoka; Mamoru Saito, Tsuruoka; Takashi Mori, Tsuruoka; Toshio Honma, Tsuruoka, all of Japan

[73] Assignee: Mizusawa Kagaku Kozyo Kabushiki Kaisha, Osaka, Japan

[21] Appl. No.: 217,084

[22] Filed: Dec. 16, 1980

Related U.S. Application Data

[63] Continuation-in-part of Ser. No. 958,490, Nov. 7, 1978, abandoned.

[30] Foreign Application Priority Data

Nov. 12, 1977 [JP] Japan ............................. 52-135908

[51] Int. Cl.³ ................ C01G 21/14; C04B 31/02; C07F 7/24
[52] U.S. Cl. ............................. 423/92; 423/305; 423/311; 423/326; 423/433; 423/512 R; 423/559; 423/593; 423/595; 423/620; 423/436; 106/297; 106/298; 106/288 Q; 260/435 R
[58] Field of Search ............... 423/433, 436, 559, 619, 423/620, 305, 311, 326, 512, 593, 595, 435, 92; 106/297, 288 Q, 298; 260/435 R

[56] References Cited

U.S. PATENT DOCUMENTS

| | | | |
|---|---|---|---|
| 481,005 | 8/1892 | Coleman | 423/620 |
| 639,209 | 12/1899 | Bunn et al. | 423/620 |
| 963,917 | 7/1910 | Meurawt | 106/297 |
| 1,617,098 | 2/1927 | Blumenberg, Jr. | 106/297 |
| 2,013,531 | 9/1935 | Applesate | 423/436 |
| 2,268,913 | 1/1942 | Turbett | 106/297 |
| 2,415,917 | 2/1947 | Stewart | 106/297 |
| 2,421,706 | 6/1947 | Kebrich | 106/297 |
| 3,700,476 | 10/1972 | Meldruor | 106/297 |
| 3,706,585 | 12/1972 | Eckert et al. | 106/297 |
| 4,117,104 | 9/1978 | Susahaka et al. | 423/619 |

*Primary Examiner*—Gary P. Straub
*Attorney, Agent, or Firm*—Sherman & Shalloway

[57] ABSTRACT

Disclosed is a process for the preparation of lead compounds which comprises reacting lead monoxide according to the wet method with an inorganic acid or organic acid in the presence of hydroxylamine under such conditions that the initial pH value of the reaction system is not higher than 7.

Lead monoxide according to the wet method has an excellent reactivity with an inorganic acid or organic acid, but it contains higher oxides such as lead dioxide and minium, which cause coloration in lead compound products. According to this process, this undesirable coloration can effectively prevented.

8 Claims, 1 Drawing Figure

PROCESS FOR PREPARATION OF LEAD COMPOUNDS

This application is a continuation-in-part application of the application Ser. No. 958,490 filed on Nov. 7, 1978, which has now been abandoned.

This invention relates to a process for preparing a lead compound from lead monoxide according to the wet method. More particularly, the invention relates to a process in which various lead compounds valuable as pigments, anticorrosive agents, thermal stabilizers and the like can be prepared substantially in the absence of a catalyst from lead monoxide according to the wet method while preventing coloration of products.

Lead salt pigments such as chrome yellow have heretofore been ordinarily prepared by double decomposition of a soluble lead salt such as lead nitrate and a corresponding alkali metal salt such as sodium chromate. This double decomposition method, however, is defective in that since an unreacted lead salt, namely a lead salt dissolved in water, is inevitably present in the mother liquor and a water-soluble salt such as dodium nitrate is included in the formed lead salt, the washing treatment should inevitably be conducted and formation of a large quantity of waste water containing lead components cannot be avoided. As means for eliminating this defect, there has already been proposed a process in which lead monoxide (litharge) is directly reacted with chromic anhydride. However, since known lead monoxide is poor in the reactivity with chromic anhydride, only a lead chromate product being very poor in the hue is obtained according to this process, and therefore, this process has not been commercially practised.

A basic lead salt valuable as a thermal stabilizer for vinyl chloride resins and the like, such as tribasic lead sulfate, is prepared by reacting lead monoxide (litharge) with an acid such as sulfuric acid in an aqueous medium containing a catalyst such as acetic acid. When a catalyst such as acetic acid is used for this reaction, the lead component in an amount equivalent to acetic acid or the like catalyst is left in the form of a water-soluble salt such as lead acetate in the reaction medium, resulting in the loss of the lead component, and moreover, the washing treatment is necessary for removal of this water-soluble salt. Accordingly, also this process involves a defect that waste water containing the soluble lead components is inevitably formed.

As is seen from the foregoing description, in the conventional processes for preparing lead compounds excellent in the hue, the stabilizing activity and other properties, it is indispensable that the lead component should be used in the form of a water-soluble salt or an acetic acid catalyst should be used for solubilizing the lead component for the reaction. Accordingly, in these conventional processes, it is impossible to eliminate the defect that the operation of washing the resulting lead compound or the operation of recovering the water-soluble lead salt from waste water should inevitably be carried out.

Lead monoxide according to the wet method, that is, ultrafine particulate lead monoxide obtained by charging granules of metallic lead in a rotary mill together with a liquid medium and oxygen and rotating the rotary mill rotated under such conditions that at least parts of the granules of metallic lead wetted with the liquid medium are located in the gas phase above the liquid level and friction is caused among the granules of metallic lead through the liquid medium, can easily react with various inorganic acids or organic acids even in the absence of a catalyst to provide desirable lead compounds. However, this lead monoxide contains higher oxides such as lead dioxide and minimum, which color the resulting lead compounds in undesirable hues and reduce the capacities and commercial values of the products.

We found that when the above-mentioned lead monoxide is reacted with an inorganic or organic acid, if an acid addition salt of hydroxylamine is made present in the reaction system and the initial pH value of the reaction system is maintained at a level not higher than 7, the hue of the resulting lead compound is remarkably improved. If lead monoxide according to the wet method is mixed with an inorganic acid or organic acid in the presence of an acid addition salt of hydroxylamine, higher oxides contained in lead monoxide are effectively reduced in situ and coloration of the product by these higher oxides can be effectively prevented.

It is therefore a primary object of this invention to provide a process for preparing lead compounds excellent in the hue, anti-corrosive action and thermal stabilizing activity directly from lead monoxide according to the wet method, which is excellent in the reactivity but contains higher oxides causing coloration, and various inorganic or organic acids.

Another object of this invention is to provide a process for preparing lead compounds valuable as pigments, anti-corrosive agents and thermal stabilizers from lead monoxide according to the wet method, which contains higher oxides such as lead dioxide and minium and various inorganic or organic acids, in which these higher oxides can effectively be reduced in situ in the reaction system without any particular operation.

In accordance with the present invention, these and other objects can be attained by a process for the preparation of lead compounds having a composition represented by the following general formula:

$$nPbO \cdot PbX_{2/x} \tag{1}$$

wherein X stands for an inorganic acid or organic acid radical, x indicates the valency of the radical X and n is a number of from 0 to 5, which comprises reacting a lead monoxide with an acidic component which is a corresponding inorganic acid, its acidic oxide, a corresponding organic acid or a functional derivative thereof selected from the group consisting of an ammonium salt and an acid anhydride, wherein the lead monoxide is a lead monoxide containing a higher lead oxide selected from the group consisting of lead dioxide and minium in an amount of 0.001 to 5% by weight based on the total weight and being obtained by charging granules of metallic lead, a liquid medium and oxygen in a rotary mill, rotating the rotary mill under such conditions that at least parts of the metallic lead granules wetted with the liquid medium are located in the gas phase above the level of the liquid medium and friction is caused among the metallic granules through the liquid medium, to thereby form a dispersion of very fine particles of lead monoxide in the liquid medium and separating the dispersion from the metallic lead granules, and wherein the lead monoxide in the form of the as-prepared dispersion is mixed with said acidic component in the presence of 0.001 to 5% by weight, based on the lead monoxide, of an acid addition salt of hydroxylamine under such conditions that the initial pH value of the mixture is maintained at a level not higher than 7.

The present invention will now be described in detail.

[Starting Lead Monoxide]

The lead monoxide that is used in this invention is ordinarily prepared according to a process comprising charging granules of metallic lead, a liquid medium and oxygen in a rotary mill, and rotating the rotary mill under such conditions that at least parts of the metallic lead granules wetted with the liquid medium are located in the gas phase above the level of the liquid medium and friction is caused among the metallic granules through the liquid medium, to thereby form a dispersion of very fine particles of lead monoxide in the liquid medium.

Referring now to FIG. 1 illustrating the principle of this process for the preparation of the starting lead monoxide, metallic lead granules 2, liquid medium 3 and oxygen gas 4 are charged in a rotary mill 1, and the rotary mill 1 is rotated in a prescribed direction indicated by an arrow, namely in the clockwise direction in FIG. 1. In this process, the amounts charged of the respective substances and the peripheral rotation speed of the rotary mill 1 are controlled so that parts 2a of metallic granules having the surface wetted with the liquid medium are exposed into the gas phase 4 above the liquid level 5 and friction is caused among the metallic lead granules 2 through the liquid medium 3.

It is believed that the following mechanism is closely associated with the feature that according to the above process, lead monoxide of the very fine particulate form can be obtained at such a high conversion as not expected from the amount of oxygen dissolved in the liquid medium, though not limited by this mechanism.

(1) At first, with rotation of the rotary mill 1 the metallic lead granules 2 are raised along the circumferential wall of the mill 1 and become exposed to the gas phase 4 above the liquid level 5, and thin layers 3a of the liquid medium 3 are formed on the surfaces of the metallic lead granules 2a exposed to the gas phase 4. Oxygen gas 4 in the gas phase 4 is readily absorbed in the thin layers 3a of the liquid medium 3 and oxidizes promptly the surfaces of the metallic lead granules 2a to form very thin film layers 6 of lead monoxide on the surfaces of the metallic lead granules 2a.

(2) Metallic granules 2b having very thin layers 6 of lead monoxide formed on the surfaces thereof are rubbed with one another through the liquid medium 3 and lead monoxide in the form of the very thin film layer 6 is dispersed into the liquid medium 3 in the form of a very fine particle 7 by this friction. At this point, the liquid medium 3 has an action of inducing and dispersing selectively very fine particles of lead monoxide into the liquid medium 3 from the surfaces of the metallic lead granules with friction among the metallic lead granules.

(3) Since lead monoxide film layers 6 thus formed are perpetually removed from the metallic lead granules 2b by mutual friction of the granules through the liquid medium, the surfaces of the metallic lead granules are always kept in the fresh and highly active state.

(4) The unit steps (1) to (3) are repeated on the metallic lead granules 2 having fresh surfaces.

In other words, the reaction system of the above process is characterized in that (1) absorption of oxygen through a so-called wetted wall and subsequent oxidation of surfaces of metallic lead granules and (2) mutual friction of metallic lead granules having oxide films formed on the surfaces thereof through the liquid medium are frequently repeated in a very short cycle.

It is believed that in the process for oxidizing metallic lead by utilizing oxygen dissolved in a liquid medium, the reaction velocity is controlled by the oxygen-absorbing speed of the liquid medium. This oxygen-absorbing speed U (g/hr) is represented by the following formula:

$$U = kA(P_1 - P_2) \qquad (2)$$

in which $P_1$ denotes the partial pressure (Kg/cm$^2$ absolute) of oxygen in the gas phase. $P_2$ denotes the partial pressure (Kg/cm$^2$ absolute) of oxygen on the surface of the liquid, A is a gas-liquid contact area (cm$^2$), and k is a theoretical absorption speed constant [g·hr$^{-1}$·(cm$^2$)$^{-1}$·(Kg/cm$^2$)$^{-1}$].

From the above formula (2), it will readily be understood that in order to increase the oxygen-absorbing speed, it may be effective to increase the gas-liquid contact area A, the theoretical absorption speed constant k and the driving force ($\Delta P = P_1 - P_2$).

In the above-mentioned reaction system, since the metallic lead granules 2a having the surfaces wetted with the liquid medium are perpetually exposed to the gas phase above the liquid level 5, it is believed that the gas-liquid contact area A is remarkably increased over the case where metallic lead granules are agitated below the liquid level and oxygen is blown into the liquid medium and that since the metallic lead granules and the liquid medium are agitated by rotation of the mill 1, the gas-liquid contact area A is further increased. It is also believed that since the layer 3a formed on the surface of the metallic lead granule is very thin and the gas phase and wetted metallic lead granules are violently agitated, interfacial films participating in migration of substances on both the gas phase and liquid phase sides are made thinner, resulting in remarkable increase of the absorption speed constant k. Thus, the reasons why such a high oxidation speed as not expected from the amount of oxygen dissolved in the liquid medium can be attained according to the abovementioned process will be apparent.

Another factor influencing the speed of oxidation of metallic lead is a surface condition of a metallic lead granule. More specifically, in the case where an oxide film is formed on the surface of granular metallic lead, the granules are rendered passive and the oxidation speed is remarkably reduced. In the above process, however, it is possible to rub violently metallic lead granules having very thin oxide films by mutual friction through the liquid medium and lead monoxide formed can be dispersed and separated very promptly into the liquid medium to render the surfaces of the metallic lead granules fresh and active, whereby the speed of oxidation of metallic lead can be remarkably enhanced.

The feature of this invention that lead monoxide formed on the surface of the metallic lead granule in the form of a very thin film is dispersed into the liquid medium by mutual friction of the metallic lead granules results in great advantages as regards not only the conversion but also the selectivity. For example, if granular metallic lead is maintained in the surface-wetted state in an oxidizing atmosphere for a long time, as illustrated in Comparative Example 6 given hereinafter, the conversion is reduced and formation of lead oxides other than lead monoxide, such as minium ($Pb_3O_4$) and/or lead peroxide ($PbO_2$), is enhanced to reduce the selectivity to lead monoxide drastically. In this case, the hue of the resulting oxide product is very bad. According to the above process, the selectivity to lead monoxide is generally at least 95%, especially at least 97%, and the resulting lead monoxide is excellent in the hue and hue stability.

Furthermore, the feature that oxidation of metallic lead is performed through the liquid medium and mutual friction of metallic lead granules is conducted through the liquid medium produce the following additional advantages:

(a) Precise control of the oxidation speed is possible and the oxide film formed on the surface of granular metallic lead can be made very thin.

(b) The liquid medium has an action of uniformalizing the oxidation temperature in the entire system and the oxidation temperature can be controlled to a very low level with the aid of the above advantage (a).

(c) The liquid medium has a much higher activity of inducing and dispersing very fine particles of lead monoxide from the surfaces of the metallic lead granules than a gaseous medium.

(d) Lead monoxide formed in the form of a very thin film can be separated from the granular metallic lead and can be stored and accumulated in the system in the form of a suspension until the concentration is elevated to a remarkably high level.

In the preparation of the starting lead monoxide used in this invention, the solid-liquid ratio ($R_{SL}$) defined by the following formula:

$$R_{SL} = W/V_1 \quad (3)$$

wherein $V_1$ is a volume (l) of the liquid medium in the rotary mill and W is an amount (Kg) of granular metallic lead in the rotary mill, is also an important factor for practising the above process under the above conditions. The lower limit of the solid-liquid ratio is determined based on whether or not wet metallic lead granules can be effectively exposed to oxygen in the gas phase. If the solid-liquid ratio is lower than the lower limit, the yield per unit time is drastically reduced. The upper limit of the above solid-liquid ratio is determined based on whether or not a wetted wall is effectively formed on granular metallic lead and effective friction can be accomplished among the granules in the liquid medium. When this solid-liquid ratio $R_{SL}$ exceeds beyond a certain critical value, the selectivity to lead monoxide is drastically reduced. It is generally preferred that the above solid-liquid ratio $R_{SL}$ be adjusted within a range of from 1 to 100 Kg/l, especially from 1 to 50 Kg/l.

Further, the gas-liquid ratio ($R_{GL}$) defined by the following formula:

$$R_{GL} = V_2/V_1 \quad (4)$$

in which $V_1$ is a volume (l) of the liquid medium in the rotary mill and $V_2$ is a volume (l) of the space of the gas phase oxygen, is also an important factor. It is generally preferred that this gas-liquid ratio ($R_{GL}$) be within a range of from 0.05 to 120, especially from 0.25 to 60. When the gas-liquid ratio ($R_{GL}$) is lower than 0.05, the gas-liquid contact area is reduced and the yield per unit time or conversion is considerably lowered. If this gas-liquid ratio ($R_{GL}$) is higher than 120, reduction of the selectivity is conspicuous.

In order to perform effectively mutual friction of metallic lead granules and attain a high agitation effect in the reaction system, it is preferred that the packed volume ratio $R_V$ defined by the following formula:

$$R_V = B/V_o \quad (5)$$

in which B is a bulk volume of metallic lead granules packed in the rotary mill and $V_o$ is an inner volume of the rotary mill, be within a range of from 0.05 to 0.4, especially from 0.06 to 0.3.

Still further, in order to manifest the abovementioned activities (1) and (2) effectively, it is important to adjust the rotation speed of the rotary mill appropriately. More specifically, in the above process, it is preferred that the rotary mill be rotated at a rotation number corresponding to 20 to 150%, especially 25 to 125%, of the critical rotation number ($N_C$, rpm) defined by the following formula:

$$N_C = 42.27/\sqrt{D} \quad (6)$$

in which D denotes an inner diameter (m) of the rotary mill. When the rotary mill is rotated at a rotation number larger than 150% of the critical rotation number, the yield of lead monoxide, namely the conversion to lead monoxide, is rather reduced, and adoption of such a large rotation number is not preferred because of wasteful consumption of energy.

Incidentally, the above critical rotation number ($N_C$) is a value theoretically determined on granules having in contact with the inner wall face of the rotary mill. Accordingly, even when the rotation number is larger than this critical rotation number, granules which have separated from the inner wall face of the rotary mill are once lifted up and when the granules are set free from the influence of the centrifugal force, they are let to fall by the gravity. In fact, by the naked eye observation we confirmed that if the rotary mill is rotated at a rotation number within the above range, granules of metallic lead fall violently on the liquid level to cause bubbling in the liquid.

According to the above process, by charging metallic lead granules, a liquid medium and oxygen in a rotary mill so that the above specific quantitative relationships are established and rotating the rotary mill at a rotation number within the above range, the oxygen absorption speed constant [Ka, $g \cdot hr^{-1} \cdot l^{-1} \cdot (Kg/cm^2)^{-1}$] defined by the following formula:

$$Ka = Uo/(P_1 \times Vo) \quad (7)$$

in which Uo is an amount of oxygen consumed per unit time (g/hr) calculated from the amount of lead monoxide formed per unit time, Vo is an inner volume (l) of the rotary mill, and $P_1$ is a partial pressure ($Kg/cm^2$ absolute) of oxygen in the gas phase in the rotary mill, can be elevated to at least 0.05, especially at least 0.1.

The form of metallic lead granules is not particularly critical, and any of spherical granules, elliptical granules, columnar granules, prismatic granules, cubic granules, granules of other polyhedral forms, granules of rod-like forms, granules of gravel-like forms and amorphous granules can be used in the above process. However, in order to perform mutual friction of the granules effectively in the liquid medium, it is preferred that granules having a large volume per unit surface area, namely a heavy weight, such as spherical and elliptical granules, be used. It has been found that in the above process, even when the form of the granular metallic lead charged is indefinite to some extent, if rotation is continued in the rotary mill, the form of the granules is changed to a substantially spherical form by the plasticity of lead. The average size of the granular metallic lead to be charged to the reaction system can be changed within a range of 0.5 to 7 mm. In general, the conversion can be effectively improved when the size of the granules is reduced to increase the surface area per unit weight of lead charged. However, if the size of the granules is too small, a high friction effect is attained in the liquid medium and the granules become massive by cohesion, and therefore, it is impossible to form wetted walls on respective granules effectively. In this invention, it is preferred that the average size of the granular metallic lead be within a range of from 0.5 to 7 mm, especially from 1 to 5 mm. Granules of metallic lead can be prepared by known methods, for example, casting, extrusion, spraying, scattering and granulation in water.

In the above process, not only as-prepared granular metallic lead having a fresh outer surface but also granular metallic lead which has been allowed to stand still and which is rendered passive by a thin film of lead oxide, basic lead carbonate or the like formed on the outer surface thereof can be used in this invention. When ordinary lead monoxide is prepared, it is possible to use any of the above-mentioned two types of lead granules, but when it is intended to prepare lead monoxide of the hydrate type, it is preferred to use granular metallic lead having a fresh metal surface. Metallic lead granules which have been rendered passive can easily be converted to granules having fresh metal surfaces by treatment with dilute acetic acid, nitric acid, hydrochloric acid or the like. In order to obtain lead monoxide excellent in the hue, it is preferred to use granules having fresh metal surfaces. It has been found that the fresh surface state can be kept for a long time if metallic lead granules having fresh metal surfaces are completely immersed in stagnant water.

In this invention, any of liquid media capable of dissolving oxygen therein and substantially inactive with metallic lead and formed lead monoxide can be used. For example, there can be used aqueous media, polar organic solvents, e.g., alcohols such as methanol, ethanol, butanol, glycerin, ethylene glycol, propylene glycol and diacetone alcohol, ethers such as diethyl ether, dioxane, tetrahydrofuran and cellosolves, ketones such as methylethyl ketone, acetone, hexanone and isophorone, esters such as ethyl acetate and amyl acetate, amides such as dimethylformamide and dimethylacetamide, sulfoxides such as dimethylsulfoxide and amines such as pyridine and dimethylaniline, and nonpolar organic solvents, e.g., benzene, toluene, xylene, tetralin, dipentene, isoparaffin, heptane, trichlene, perchlene, chloroform, methylene chloride and carbon tetrachloride.

In practising the above process, it is preferred to use polar solvents, especially water and aqueous media such as mixtures of water with water-miscible polar organic solvents such as mentioned above. Water is a stable liquid medium which is available at a cheapest cost and water is excellent in the property of dissolving oxygen therein. Further, water has a high activity of inducing and dispersing formed lead monoxide in the very fine particulate state, and when water is used as the liquid medium, a dispersion of lead monoxide formed can be recovered in a stable state and at a high lead monoxide concentration. Accordingly, use of water as the liquid medium is most preferred. Further, use of water produces an advantage that the temperature of the treatment system can be changed within a relatively broad range. It is desirable to use water singly as the liquid medium, but if desired, a water-miscible organic solvent such as an alcohol, an ether and a ketone can be used together with water in an amount of up to 50 parts by volume, especially up to 40 parts by volume, per 100 parts by volume of water.

The reaction proceeds smoothly even in the absence of a catalyst. However, in order to adjust the conversion of metallic lead to lead monoxide per unit time or control the crystal form of the resulting lead monoxide, various catalysts may be added to the liquid medium. As the catalyst, there can be mentioned, for example, (1) acids, e.g., inorganic acids such as nitric acid and organic acids such as acetic acid, (2) alkaline agents, e.g., ammonia, alkali metal hydroxides such as sodium hydroxide, alkaline earth metal hydroxides, and organic bases such as amines, and (3) salts such as ammonium nitrate, ammonium acetate, quaternary ammonium salts and acid addition salts of amines, but catalysts that can be used are not limited to those recited above. The amount added of the catalyst is not particularly critical. In general, the catalyst may be present in the liquid medium in an amount of $5 \times 10^{-4}$ to 5% by weight based on the liquid medium, especially 0.01 to 3% by weight based on the liquid medium.

Molecular oxygen alone or a mixture of molecular oxygen with an inert gas can be used for oxidizing metallic lead in the above process. As the inert gas, there can be mentioned, for example, nitrogen, helium and argon. In order to increase the solubility of oxygen in the liquid medium, it is preferred to use pure oxygen gas, but better results are obtained when a gaseous mixture comprising 1 mole of oxygen and up to 10 moles, especially up to 5 moles, of an inert gas such as nitrogen is employed. Accordingly, decarbonated air or a mixture of decarbonated air and oxygen can be used in the above process. The pressure of oxygen or an oxygen-containing gas that is used may be atmospheric, but it is generally preferred that the pressure of oxygen or the oxygen-containing gas be elevated to at least 0.2 $Kg/cm^2$ (absolute), especially to 1 to 10 $Kg/cm^2$ (absolute). In order to enhance the speed of absorption of oxygen into the liquid medium, as will be apparent from the above formula (2), it is preferred to increase the partial pressure of oxygen in the gas phase.

In practising the above process, the temperature of the reaction system, especially the temperature of the liquid medium, is not particularly critical, so far as the temperature is higher than the melting point of the liquid medium used and lower than the boiling point thereof under the reaction conditions adopted. Of course, oxidation reaction of metallic lead is an exothermic reaction. Accordingly, if the milling treatment is conducted batchwise for a long time, the temperature is gradually elevated. Preferred temperatures differ to some extent depending on the intended crystal form of lead monoxide, but in general, it is preferred that the temperature be maintained within a range of from $-5°$ to $70°$ C. especially from $0°$ to $50°$ C. When the temperature of the liquid medium is relatively high, the theoretical oxygen absorption constant (k) tends to decrease, and the selectivity is often reduced and the hue of the resulting lead monoxide is degraded in some cases. Accordingly, in practising the above process, it is preferred that the reaction system be cooled directly or the liquid medium to be fed to the reaction system be cooled in advance.

The oxidation may be conducted batchwise or in a continuous manner. For example, prescribed amounts of granular metallic lead, a liquid medium and oxygen or an oxygen-containing gas are charged into the above-mentioned rotary mill and the reaction can be conducted batchwise. In this case, oxygen or the oxygen-containing gas may fed into the rotary mill intermittently or continuously. Alternately, prescribed amounts of granular metallic lead and the liquid medium are charged in the rotary mill, and then, oxygen or the oxygen-containing gas and the liquid medium are fed intermittently or continuously while a slurry containing ultrafine particles of lead monoxide is withdrawn intermittently or continuously. In this continuous method, the granules of metallic lead may be charged into the rotary mill intermittently or continuously.

The residence time of the liquid medium in the reaction system, namely the time for contact of the liquid medium with metallic lead granules under mutual friction through the liquid medium, is not particularly critical. In the above process, lead monoxide formed according to the above-mentioned mechanism is exfoliated and dispersed in the liquid medium in a short time, but when the contact time is too short, only a dispersion (slurry) having a very low lead monoxide concentration is formed. Accordingly, it is generally preferred that the contact time be adjusted to at least 0.5 minute, especially 1 to 120 minutes. Of course, even when the residence time of the liquid medium in the reaction system is lower than the above range, a concentrated dispersion can be obtained by recycling the dispersion of a low concentration recovered from the reaction system, to the reaction system directly or after it has been cooled. If lead monoxide formed is made resident in the reaction system for too long a time, the hue of the product is degraded or the selectivity is reduced. Accordingly, it is not preferred to make formed lead monoxide resident in the reaction system for too long a time.

In practising the above process, the concentration of lead monoxide in the slurry to be recovered from the reaction system can be controlled to 0.1 to 35 g/100 cc, especially 0.3 to 20 g/100 cc. It is one of significant advantages of the above process that a slurry of lead monoxide having such a high concentration can be recovered.

Accordingly, ultrafine particles of lead monoxide are exfoliated and dispersed in the liquid medium and a dispersion of these ultrafine particles is formed. Separation of this lead monoxide dispersion from the metallic lead granules can be accomplished very easily only by withdrawing the dispersion from the reaction system. It is another advantage of the above process that this separation can be accomplished without particularly adopting any solid-liquid separation operation, for example, filtration, centrifugal separation, decantation or spray drying. Furthermore, it is very advantageous that the thus recovered dispersion or slurry is substantially free of metallic lead or other impurities. Of course, in the case where the size of metallic lead granules is drastically reduced, incorporation of ultrafine particles of metallic lead into the recovered lead monoxide dispersion can be completely prevented by passing the dispersion through a separator such as a liquid cylone.

The separated dispersion or slurry may be used as a raw material for production of various lead salt compounds as it is, but if desired, ultrafine particles of lead monoxide can be separated in the form of powder from the slurry. For example, the lead monoxide is first recovered in the form of a cake by sedimentation, centrifugal separation, decantation, filtration, electrophoresis, spray drying or the like and a final powdery product can be obtained by drying this cake.

Addition of an acid, a base or a salt thereof or a coagulant to the dispersion is effective for accelerating flocculation and sedimentation of ultrafine particles of lead monoxide and facilitating the solid-liquid separation.

Lead monoxide that is used in this invention can be clearly distinguished from known lead monoxides in the point that is has a true density of 8.3 to 9.2 g/cc, preferably 8.35 to 9.18 g/cc. For example, Gmerin's Handbüch teaches that known yellow PbO of the rhombic system has a density of 9.63 g/cc and known red PbO of the tetragonal system has a density of 9.34 g/cc. The lead monoxide that is used in this invention has a considerably lower true density than known lead monoxides. This suggests that in the lead monoxide of this invention the atomic distance between lead and oxygen atoms is larger than in known lead monoxides.

It is believed that the reason why the lead monoxide can have a density in such a broad range as of from 8.3 to 9.2 g/cc is that the density is changed depending on the crystal form or the mixing state of crystal forms.

In the instant specification, by the term "litharge type lead monoxide (L)" is meant a lead monoxide having X-ray diffraction peaks substantially corresponding to the following X-ray diffraction pattern:

TABLE A

| Lattice Spacing d (Å) | Relative Intensity (I/Io) |
|---|---|
| 5.03 | 7.2 |
| 3.11 | 100 |
| 2.81 | 38.6 |
| 2.51 | 20.5 |
| 1.98 | 29.8 |
| 1.67 | 25.5 |
| 1.55 | 10.0 |
| 1.54 | 14.2 |

Further, in the instant specification, by the expression "substantially corresponding" is meant the fact that each of values of the relative intensity of peaks of the lead monoxide may be changed from the value given above within a range of ±2%.

By the term "massicot type lead monoxide (M)" used herein is meant a lead monoxide having X-ray diffraction peaks substantially corresponding to the following X-ray diffraction pattern:

TABLE B

| Lattice Spacing d (Å) | Relative Intensity (I/Io) |
|---|---|
| 3.07 | 30.5 |
| 2.95 | 100 |
| 2.74 | 7.4 |
| 2.38 | 5.2 |

By the term "hydrate type lead monoxide (H)" used herein is meant a lead monoxide having X-ray diffraction peaks substantially corresponding to the following X-ray diffraction pattern:

TABLE C

| Lattice Spacing d (Å) | Relative Intensity (I/Io) |
| --- | --- |
| 3.67 | 100 |
| 3.38 | 34.6 |
| 3.14 | 11.6 |
| 3.05 | 74.3 |
| 2.95 | 11.6 |
| 2.91 | 17.1 |
| 2.86 | 75.6 |
| 2.55 | 34.9 |
| 2.46 | 21.1 |
| 2.33 | 20.4 | or a composition composed mainly of this lead monoxide and containing a small amount of the litharge type lead monoxide and/or the massicot type lead monoxide.

Lead monoxide of the above-mentioned litharge type crystal structure has a density of 8.80 to 9.17 g/cc, lead monoxide of the massicot type crystal structure has a density of 8.35 to 9.2 g/cc, and lead monoxide of the hydrate type crystal structure has a density of 8.80 to 9.1 g/cc.

The lead monoxide that is used in this invention generally has an average particle size not larger than $0.2\mu$, especially not larger than $0.1\mu$. From an electron microscope photograph, described hereinafter, of known yellow PbO of the rhombic system, it is seen that the average particles size of this known lead monoxide is in the range of from 2 to $5\mu$.

Further, from an electron microscopic photograph of known red lead monoxide of the tetragonal system, it is seen that the average particle size of this known lead monoxide is in the range of from 3 to $5\mu$. In contrast, the novel lead monoxide that is used in this invention has a much finer average particle size. More specifically, from electron microscope photographs of instances of the novel lead monoxide that is used in this invention, it is seen that the average particle size of the litharge type lead monoxide is 0.01 to $0.05\mu$, that of the massicot type lead monoxide is 0.01 to $0.05\mu$, and that of the hydrate type lead monoxide is also 0.01 to $0.05\mu$.

The lead monoxide that is used in this invention is further characterized in that it has an infrared (IR) absorption peak at a wave number of 1400 to 1410 cm$^{-1}$. Any of known yellow PbO of the rhombic system and known red PbO of the tetragonal system has not substantially an absorption peak at a wave number of 1400 to 1410 cm$^{-1}$. In contrast, all of the litharge type lead monoxide that is used in this invention, the massicot type lead monoxide that is used in this invention and the hydrate type lead monoxide that is used in this invention have a prominent peak at a wave number of 1400 to 1410 cm$^{-1}$. Further, each of the lead monoxides used in this invention has a sharp absorption at a wave number of about 680 cm$^{-1}$.

As a lead compound having IR absorption peaks at wave numbers of about 1400 cm$^{-1}$ and about 680 cm$^{-1}$, there is known so-called lead carbonate. However, each of the lead monoxides that are used in this invention is clearly distinguished from this lead carbonate. More specifically, each of lead monoxides mentioned above is one prepared in the reaction system from which carbon dioxide is completely excluded under such reaction conditions that no lead carbonate can be formed. Further, the lead monoxides used in this invention are substantially free of IR absorption peaks inherent of lead carbonate, for example, peaks at wave numbers of 840, 1052 and 1732 cm$^{-1}$, and they have an IR absorption peak at a wave number of about 490 cm$^{-1}$, which is not observed at all in the IR absorption spectrum of lead carbonate. Accordingly, it can be said that the above-mentioned two absorption peaks are absorption peaks inherent of the novel lead monoxide that is used in this invention.

The lead monoxide that is used in this invention can also be distinguished from known lead monoxides in the point that the lead monoxide has a chromic anhydride reactivity of at least 94%, preferably at least 96%. The term "chromic anhydride reactivity (RC)" used herein means a value defined by the following formula:

$$RC (\%) = \frac{AC}{TC} \times 100 \qquad (8)$$

wherein AC denotes the quantitative analysis value (g) of CrO$_3$ in a product (lead chromate) obtained by reacting lead monoxide with chromic anhydride at a molar ratio of 1:1 in water in the absence of a catalyst at 60° to 70° C., and TC denotes a theoretical value (g) of CrO$_3$ to be contained in the product, namely the amount of chromic anhydride added. A higher value of the chromic anhydride reactivity indicates that reaction is performed more effectively.

Known lead monoxides generally have a chromic anhydride reactivity ranging from 40 to 80%, though the value varies to some extent according to the preparation method. Accordingly, they cannot be used for production of chrome yellow and the like if a catalyst is not used. In contrast, the lead monoxide that is used in this invention has such a high chromic anhydride reactivity (RC) as cannot be expected from the values of known lead monoxides, for example, 99.9%.

The lead monoxide that is used in this invention can take any of the above-mentioned litharge, massicot and hydrate type crystal forms according to the preparation conditions. The litharge type lead monoxide has a hue of a light yellow (light lemon) to orange color which varies depending on the preparation conditions. From the fact that orange litharge type lead monoxide produces a minute amount of dark turbidity when dissolved in acetic acid, it has been confirmed that it contains a minute amount of lead peroxide and/or minium. It has also been confirmed that light lemon litharge type lead monoxide is substantially free of lead peroxide or minium. The litharge type lead monoxide that is used in this invention resembles known red PbO of the tetragonal system in the point that it has substantially the above-mentioned X-ray diffraction pattern shown in Table A. The litharge type lead monoxide that is used in this invention can be clearly distinguished from this known PbO by the above-mentioned various characteristics, and it is different from the known PbO also in the point that the litharge type lead monoxide that is used in this invention has a light yellow hue, whereas the known PbO has a sharp scarlet hue.

The massicot type lead monoxide that is used in this invention having substantially the above-mentioned X-ray diffraction pattern shown in Table B generally has a yellow hue, and it is not particularly different from the known yellow PbO of the rhombic system with respect to the hue and the X-ray diffraction pattern, but it can be clearly distinguished from the known yellow PbO with respect to the above-mentioned various characteristics, especially the reactivity.

From the fact that the hydrate type lead monoxide having substantially the above-mentioned X-ray diffraction pattern shown in Table C has a white hue and it is transformed into massicot type lead monoxide when dried completely, it has been identified as hydrous lead monoxide. In the hydrate type lead monoxide that is used in this invention, the content of hydrate water is 0.2 to 0.8 mole, especially 0.3 to 0.5 mole, per mole of PbO.

In the novel lead monoxide that is used in this invention, since the above-mentioned peculiar preparation process is adopted, there is attained an advantage that the metallic lead content is remarkably reduced. Lead monoxide prepared from lead suboxide according to the so-called powder method has a metallic lead content of an order of 0.01 to 3% as expressed as the acetic acid-insoluble component content. In contrast, in the novel lead monoxide that is used in this invention, the metallic lead content is so low that the presence of metallic lead can hardly be analytically confirmed.

The litharge type lead monoxide that is used in this invention can be prepared very easily under the above-mentioned reaction conditions. For example, it can readily be prepared under an oxygen pressure of 0.2 to 6 Kg/cm$^2$ (absolute) at a temperature of $-5°$ to 60° C. for a residence time of 5 to 60 minutes in the absence or presence of a catalyst.

The massicot type lead monoxide that is used in this invention can be prepared, for example, under an oxygen pressure of at least 1 Kg/cm$^2$ (absolute), preferably in the presence of 0.001 to 8% by weight, based on the liquid medium, of acetic acid as a catalyst, by using water as the liquid medium.

Further, the hydrate type lead monoxide that is used in this invention can be prepared by using metallic lead granules having fresh metal surfaces, water as the liquid medium and acetic acid or ammonium nitrate as a catalyst and by adopting a relatively low reaction temperature, for example, $-5°$ to 30° C.

As is seen from a very high chromic anhydride reactivity, the lead monoxide according to the wet method is advantageous in that it can easily react with various acids or reactive derivatives thereof even in the absence of a catalyst to provide corresponding lead compounds in high yields. However, this lead monoxide contains higher oxides formed as by-products, such as blackish brown or black lead dioxide and vermilion minium, in an unnegligible amount, that is, 0.001 L to 5% by weight, especially 0.01 to 3% by weight, based on the lead monoxide, and these higher oxides causes a problem of undesirable coloration of the resulting lead compounds.

According to the present invention, this undesirable coloration of final lead compound products can be prevented by very simple means described below.

[Reaction of Lead Monoxide with Inorganic or Organic Acid]

According to the present invention, in reacting the above-mentioned lead monoxide according to the wet method with an inorganic acid, its acidic oxide, an organic acid or a functional derivative thereof such as an ammonium salt or acid anhydride, an acid addition salt of hydroxylamine is made present in an amount of 0.001 to 5% by weight, especially 0.01 to 2% by weight, particularly preferably 0.03 to 1% by weight, based on the lead monoxide, and the initial pH value at the step of mixing both the starting materials is maintained at a level not higher than 7, preferably not higher than 6.5. It is sufficient if this pH value is maintained only for several seconds, and good results are obtained if the time during which the above initial pH value is maintained is at least 5 seconds, especially at least 10 seconds.

For example, even when the intended lead compound is a basic salt such as tribasic lead sulfate, if lead monoxide is mixed with sulfuric acid in the presence of water, the pH value of the mixture is once reduced violently below 7, and with advance of the reaction, the pH value is gradually increased exceeds 7 in a short time, and finally, the pH value becomes 7.5 to 8.5. According to the present invention, this reduction of the pH value for a short time at the mixing step is utilized for reduction of higher oxides of lead by hydroxylamine.

An acid addition salt of hydroxylamine is a known reducing agent, but this reducing agent has no reducing activity if the reaction mixture is alkaline. The lead monoxide in the form of an aqueous slurry obtained according to the above-mentioned wet method is considerably basic, and the pH value of this slurry is ordinarily in the range of from 9.8 to 10.5. Therefore, even if an acid addition salt of hydroxylamine is added to this lead monoxide aqueous slurry, PbO$_2$ or Pb$_3$O$_4$ contained in the starting lead monoxide is hardly reduced.

In contrast, according to the present invention, an acid component added as the reactant activates the acid addition salt of hydroxylamine present in the reaction system before the acid component acts as the reactant, and PbO$_2$ or Pb$_3$O$_4$ contained in the starting lead monoxide is effectively reduced by the so activated acid addition salt of hydroxylamine. It is quite an unexpected finding that reduction of PbO$_2$ or Pb$_3$O$_4$ by hydroxylamine is effectively accomplished in such a short time as several seconds.

The intended lead compound of the present invention is represented by the following formula:

$$nPbO \cdot PbX_{2/x} \qquad (1)$$

wherein X stands for an inorganic acid or organic acid radical, x indicates the valency of the radical X and n is a number of from 0 to 5.

In the instant specification and claims, by the term "acidic oxide" is meant an oxide formed by removing water from an inorganic acid, such as chromic anhydride (CrO$_3$), and by the term "functional derivative" is meant a derivative of an inorganic acid or organic acid having a reactivity substantially equal to the reactivity of the acid, such as an ammonium salt or acid anhydride.

In the above general formula, as the inorganic acid, there can be mentioned, for example, oxyacids of sulfur such as sulfuric acid and sulfurous acid, oxyacids of phosphorus such as phosphoric acid and phosphorus acid, carbonic acid, oxyacids of chromium such as chromic acid, oxyacids of molybdenum such as molybdic acid, oxyacids of tungsten such as tungstic acid, and silicic acid. These inorganic acids may be used singly or in the form of a mixture of two or more of them. A dibasic or tribasic oxyacid is ordinarily preferred as the inorganic acid.

As the organic acid, there can be mentioned, for example, aromatic carboxylic acids such as phthalic acid, isophthalic acid, terephthalic acid, benzoic acid, salicylic acid, p-hydroxybenzoic acid, naphthoic acid, naphthalene-dicarboxylic acid, and biphenyl-dicarboxylic acid, aliphatic and alicyclic carboxylic acids such as maleic acid, fumaric acid, itaconic acid, 2-ethylhexanoic acid, palmitic acid, stearic acid, oleic acid, linoleic acid, oxo-process branched fatty acids, Koch-process neoacids, naphthenic acid, hexahydroterephthalic acid and tetrahydrophthalic acid, and cyanamide. These organic acids may be used singly or in the form of a mixture of two or more of them. A dibasic carboxylic acid or a monobasic carboxylic acid having at least 2 carbon atoms is preferred as the organic acid.

The lead compound represented by the general formula (1) may be an ortho-salt such as lead chromate or a basic salt such as tribasic lead sulfate. Further, it may be a salt containing at least two acid radicals, such as lead silicosulfate.

Suitable examples of the lead compound represented by the general formula (1) include monobasic lead sulfate ($PbO.PbSO_4$), tribasic lead sulfate ($3PbO.PbSO_4.H_2O$), tetrabasic lead sulfate ($4PbO.PbSO_4$), basic lead silicate ($PbO.2PbSiO_3$), basic lead silicosulfate (consisting of a core of silica and a coating of a mixture of $3PbO.PbSiO_3$ and $PbO.PbSO_4$), dibasic lead phosphite ($2PbO.PbHPO_3, \frac{1}{2}H_2O$), basic lead carbonate [$Pb(OH)_2.2PbCO_3$], dibasic lead phthalate [$2PbO.(C_6H_y(COO)_2Pb)$], dibasic lead maleate

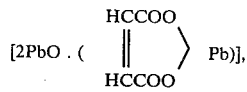

lead stearate [$(CH_3(CH_2)_{16}.COO)_2Pb$], dibasic lead stearate $\{2Pb[(CH_3.(CH_2)_{16}.COO)_2Pb]\}$, chrome yellow [($PbCrO_4$), ($3.2PbCrO_4.PbSO_4$) or ($1.5PbCrO_4.PbSO_4$)], chrome orange ($PbO.PbCrO_4$), lead silicochromate (consisting of a core of silica and a coating of $PbCrO_4$), molybdate orange ($25PbCrO_4.4PbMoO_4.PbSO_4$) and lead cyanamide [$Pb(CN)_2$]. Of course, the intended compounds of this invention are not limited to the lead compounds recited above.

The starting lead monoxide can be used for the reaction in the form of the as-prepared aqueous slurry, or in the form of a wet cake recovered from the aqueous slurry.

Even when the inorganic acid, its acidic oxide, the organic acid or functional derivative thereof that is used for the reaction is insoluble in water, if its salt is water-soluble or water-dispersible, such water-soluble or easily water-dispersible salt may be used for the reaction. For example, in case of molybdic acid, tungstic acid and carboxylic acids such as phthalic acid and stearic acid, they may be added in the form of an aqueous solution of a water-soluble or water dispersible salt, such as an ammonium salt, to the aqueous slurry of the starting lead monoxide. In this case, if the acid or acidic oxide is used in the form of an ammonium salt, there is attained an advantage that the corresponding lead compound can be obtained without performing neutralization of the alkaline component or water washing.

As the acid addition salt of hydroxylamine, there can be used, for example, hydroxylamine sulfate and hydroxylamine hydrochloride. The acid addition salt of hydroxylamine may be mixed with the starting lead monoxide in advance or with the acid component to be used in advance.

When the acid component to be used is an inorganic acid or its acidic oxide, as described hereinbefore, only by mixing both the reactants, the acidic condition is produced. On the other hand, when the acid component is an ammonium salt or the like, an acidic condition is produced in the mixture by adding an acid exerting a catalytic action, such as acetic acid, separately from this acidic component.

It is preferred that the acid addition salt of hydroxylamine as the reducing agent be used in combination with a known reducing assistant. As such reducing assistant, there can be mentioned, for example, hydrocarboxylic acids such as tartaric acid, citric acid and gallic acid, saccharides such as glucose, ascorbic acid and sucrose, and urea and urea derivatives. It is preferred that the reducing assistant be used in an amount of 0.05 to 10% by weight, especially 0.05 to 5% by weight, particularly especially 0.05 to 3% by weight, based on the lead monoxide.

Conditions for reaction of lead monoxide with the acid component are known, and these known conditions can be adopted in the present invention.

When the acid or acidic oxide used for the reaction with lead monoxide is a water-soluble compound such as sulfuric acid, phosphorous acid, chromic anhydride or cyanamide, it is preferred that an aqueous slurry of the lead monoxide according to the wet method be prepared and the reaction be carried out under agitation by adding an aqueous solution of the acid or acidic oxide to this aqueous slurry. In this case, an aqueous slurry having a lead monoxide concentration of 1 to 30% by weight is preferred, and an aqueous solution of the acid or acidic oxide having a concentration of 0.5 to 20% by weight is preferably employed. The reaction temperature is not particularly critical, and an appropriate temperature is chosen within the range of 0° to 100° C., especially 20° to 90° C., according to the kind of the intended lead compound. For example, it is preferred that the reaction be carried out at 65° to 75° C. in case of tribasic lead sulfate, at a temperature higher than 95° C. but lower than the boiling point of the reaction mixture in case of tetrabasic lead sulfate, at 60° to 70° C. in case of dibasic lead phosphite, at 60° to 70° C. in case of chrome yellow or at a temperature ranging from room temperature to 40° C. in case of lead cyanamide. Furthermore, it is preferred that the reaction of the lead monoxide with water-soluble organic acid salt be carried out at 20° to 100° C.

It is preferred that the acid addition salt of hydroxylamine, optionally together with the reducing assistant, be first added to the lead monoxide aqueous slurry or the acid component to be used for the reaction at room temperature, and then, both the reactants be mixed and the temperature of the mixture be elevated to the above-mentioned reaction mixture.

It has been found that when the acid addition salt of hydroxylamine is used singly or in combination with the reducing assistant, not only the hue but also pigment characteristics of the resulting lead compound can be improved. For example, it has been found that tribasic lead sulfate prepared from the lead monoxide by using an acid addition salt of hydroxylamine singly has a very fine particle size and it is an opaque white pigment having a remarkably high whiteness. It has also been found that tribasic lead sulfate prepared from the lead monoxide by using an acid addition salt of hydroxylamine in combination with a reducing agent such as mentioned above is a pigment having a very fine particle size and a high transparency. Of course, in each case, the particle size of the formed pigment can be increased by adding an acetic acid catalyst to the reaction system.

In the case where a product consisting of a silica core and a lead salt coating, such as lead silicosulfate or lead silicochromate, is prepared, the lead monoxide and the silicic acid component are sufficiently mixed and pulverized in the presence of water and an aqueous solution of the corresponding acid or acidic oxide is added to the resulting homogeneous mixture to effect the intended reaction.

Instead of the method in which an aqueous solution of the acid or the like is added to an aqueous slurry of the novel lead monoxide, there may be adopted a method in which an aqueous slurry of the lead monoxide is added to an aqueous solution of the acid or the like to effect the intended reaction. Further, the reaction may be accomplished by a method in which an aqueous solution of the acid or the like and an aqueous slurry of the novel lead monoxide are simultaneously poured into a reaction vessel filled with water. The reaction may be conducted batchwise or in a continuous manner. At any rate, it is important that the acid addition salt of hydroxylamine should be added to the starting material mixture and the initial pH value should be maintained at a level not higher than 7.

The resulting lead compound may be aged under heating to adjust the particle size or other properties according to need. The resulting lead monoxide is separated from the mother liquor and it is dried directly or after water washing if necessary. Thus, the final product is obtained. When the separated mother liquor or washing liquor is recycled to the reaction, discharge of lead-containing waste water can be prevented.

The present invention will now be described in detail with reference to the following Examples that by no means limit the scope of the present invention.

REFERENTIAL EXAMPLE

Metallic lead granules prepared according to the following method and classified to have a size of 1 to 6 mm were used as starting metallic lead granules for the lead monoxide to be used for the process of the present invention.

As the starting lead there was used so-called electrolytic lead having the following composition (weight ratio):

| | |
|---|---|
| Ag | 0.0001/1,000,000 |
| Cu | 0.0001/100 |
| Zn | 0.0001/100 |
| Fe | 0.0001/100 |
| Ni | — |
| Sn | 0.0005/100 |
| Bi | 0.0006/100 |
| As | 0.0001/100 |
| Pb | above 99.99/100 |

An ingot (about 50 Kg per piece) of this starting lead was charged in a vessel composed of cast iron and molten at about 350° to about 400° C. Separately, a bowl-type iron vessel having 20 holes having a diameter of 1 to 2 mm perforated in the bottom thereof was attached to a vibrating machine so that electric vibrations were given to the iron vessel at a frequency of 3000 vibrations per minute, and the iron vessel was set at a point 10 cm above the liquid level of a receiving tank filled with water maintained at about 40° to about 70° C. The molten metal was poured in the perforated iron vessel. Vibrations were given to metallic lead streams coming from the holes of the vessel and the streams were cut while falling toward the liquid level. When the molten lead was let to fall into water, it was divided into spheres having a diameter of about 1 to about 6 mm and solidified in water to form spherical granules of metallic lead.

As the apparatus for preparing lead monoxide directly from the so prepared granular metallic lead by oxidation in water, there was chosen a stainless steel rotary mill of the wet pulverization type described below, and there was adopted a method in which lead monoxide was continuous prepared by using this rotary mill.

The rotary mill used was a stainless steel tube mill having an inner diameter of 34.5 cm, a length of 130 cm and an inner volume of about 120 liters, and it was designed so that it could resist a pressure of 10 Kg/cm² gauge. A manhole of the square shape having a side of about 20 cm was formed at the center of this tube mill for cleaning of the inside of the mill and supply of raw materials, and a lid capable of resisting a pressure of 10 Kg/cm² gauge was attached to this manhole. A stainless steel pipe having an inner diameter of ½ inch was connected to one end plate of the tube mill through a rocky joint as a liquid medium introduction opening, so that the liquid medium was fed under pressure into the tube mill by a diaphragm pump of 3 horse powers. Another stainless steel pipe having an inner diameter of ½ inch was connected to the other mirror plate of the tube mill through a rocky joint as a product slurry withdrawal opening. The top end of the withdrawal pipe was inserted in the tube mill so that it was positioned below the level of the liquid medium in the tube mill and the product slurry could be withdrawn from the inside of the tube mill by the action of the inside pressure. A stainless steel wire was disposed at in the tube mill at a point closer to the center of the tube mill than the position of the above top end of the withdrawal pipe. Cooling water was showered onto the outside of the tube mill so that the entire of the tube mill was cooled. A motor of 1 horse power was connected to the tube mill through gear wheels, and a non-stage transmission apparatus was disposed so that the rotation number of the tube mill could be changed within a range of 20 to 100 rpm.

A liquid cyclone was attached to the discharge opening of the tube mill so as to prevent unreacted finer granules of metallic lead from being incorporated into the discharged dispersion.

The above tube mill was charged with 200 Kg of metallic lead granules having a size of about 1 to about 6 mm, which were prepared according to the method described above and had fresh surfaces, through the manhole formed at the center of the tube mill. Water or an aqueous solution of acetic acid having a concentration indicated in Table 1 and maintained at a temperature indicated in Table 1, if necessary, by cooling was chosen as the liquid medium. Cooling water maintained at a predetermined temperature was showered on the outside of the tube mill so that the predetermined reaction temperature was maintained in the tube mill. In the first place, the tube mill was rotated at a rotation number of 50 rpm and 30 l of water or the above acetic acid solution was charged into the tube mill, so that the solid-liquid ratio of the granular metallic lead and the aqueous medium was about 6.6. Then, cooled water or acetic acid solution was poured into the tube mill at a rate of 1 l/min and the dispersion in an amount corresponding to the amount of the thus poured aqueous medium was discharged from the tube mill. Simultaneously, oxygen ($O_2$) stored in an oxygen bomb was charged into the tube mill so that an inside pressure (gauge) indicated in Table 1 was maintained in the tube mill, and feeding of oxygen was continued that the inside pressure was maintained at the above level during the oxidation reaction. When the oxidation reaction was continued for 30 minutes, the resulting dispersion containing lead monoxide was recovered.

The so recovered lead monoxide dispersion was passed through a liquid cyclone to remove unreacted granules of metallic lead therefrom.

In the foregoing manner, 6 kinds of lead monoxide dispersions (A-1 to A-6) were prepared. With respect to each of the so formed dispersions, the amount recovered of the dispersion and the PbO concentration (inclusive of higher lead oxides contained) of the recovered dispersion were measured, and from these results, the amount formed of PbO, oxygen absorption speed constant, conversion to PbO, selectivity to PbO and the content of higher lead oxides ($PbO_n$ in which n is a number larger than 1) were determined according to the methods described below. Further, the hue of the recovered dispersion was examined, and the number average particle size of the formed lead monoxide was determined. The obtained results are shown in Table 1.

When the above-mentioned continuous oxidation reaction was conducted for 24 hours, it was found that the obtained results were not different from the results obtained when the reaction was conducted for 30 minutes.

Then, the dispersions were subjected to solid-liquid separation using a centrifugal separator. The resulting cakes were dried at 50° C. under reduced pressure to obtained novel ultrafine lead monoxide powders excellent in reactivity and light resistance (samples A-1 to A-6), and with respect to each of the resulting lead monoxide powders, nine items were checked according to the methods described below. Results of the checking on the above 15 items are shown in Table 1.

Test Methods (A) Amount (g/hr) Formed of Lead Monoxide (PbO)

From results of the analytical measurement of the amount (ml) of the dispersion recovered by 30 minutes' oxidation reaction and the concentration (g/100 ml) of lead monoxide (PbO) in the dispersion, the amount (g) formed of lead monoxide (PbO) was directly determined. From the so determined value, the amount of PbO formed by 60 minutes' reaction was calculated. The amount of higher lead oxides is included in the so determined amount of PbO.

The quantitative analysis of lead oxides was carried out according to the method of JIS K-1456.

(B) Oxygen Absorption Speed Constant (Ka)

The oxygen absorption speed constant was determined from the amount (g/hr) of oxygen consumed per unit time, calculated from the amount formed of PbO, the inner volume (l) of the rotary mill and the partial pressure ($Kg/cm^2$ absolute) of oxygen in the gas phase in the rotary mill according to the above-mentioned formula (7).

(C) Conversion (%) to Lead Oxides

In order to know amounts of lead compounds formed from metallic lead by oxidation for a unit time (60 minutes), the conversion (%) of metallic lead was determined. More specifically, from the amount (Kg) of the granular metallic lead charged and the amount (g) of the granular metallic lead consumed for the reaction, the conversion (%) was calculated according to the following formula (9):

$$\text{Conversion (\%)} = \frac{\text{amount of metallic lead consumed for reaction}}{\text{amount charged of metallic lead}} \times 100 \quad (9)$$

(D) Selectivity (%) to Lead Monoxide (PbO)

In order to compare the amount formed of lead monoxide with amounts formed of other lead compounds capable of being formed by the above reaction, such as minium ($Pb_3O_4$), lead carbonate ($PbCO_3$) and white lead [$2PbCO_3 \cdot Pb(OH)_2$], the selectivity to lead monoxide was determined. All the lead compounds contained in the recovered lead oxide dispersion were dissolved in a nitric acid-hydrogen peroxide solution, and amounts (as calculated as Pb) of minium and white lead were determined according to the method of JIS K-1457 [determination of minium ($Pb_3O_4$)] and the method of JIS K-5103 (determination of white lead) and these determined amounts were reduced from the total amounts of lead compounds in the recovered dispersion to determine the amount (as calculated as PbO) of lead monoxide. Then, the selectivity to lead monoxide was calculated according to the following formula (10):

$$\text{Selectivity (\%)} = \frac{\text{amount of lead monoxide as calculated as metallic lead}}{\text{amount of metallic lead consumed for reaction}} \times 100 \quad (10)$$

(E) Determination of Higher Lead Oxides ($PbO_n$)

A 300-ml capacity flask was charged with 5 g, precisely weighed, of lead monoxide dried at 105° C. for 2 hours, and 100 ml of pure water and 10 ml of concentrated acetic acid were added and the mixture was heated to form a solution. Then, 25 g of sodium acetate ($CH_3COONa \cdot 3H_2O$) was dissolved in the solution and 20 ml of a 1/10 N aqueous solution of sodium thiosulfate ($Na_2S_2O_3$) was added to the solution. Then, the flask was plugged and the solution was allowed to stand in the cold dark place for 30 to 40 minutes.

The solution was titered with a 1/10 N aqueous solution of iodine by using a 5% solution of starch as an indicator, and when the color of the solution was changed to violet, titration was stopped. The concentration (%) of $PbO_n$ was calculated according to the following formula:

$$PbO_n (\%) = \frac{(af_1 - af_2) \times 0.03428}{S} \times 100$$

wherein a stands for the amount (ml) of the 1/10 N $Na_2S_2O_3$ solution, b stands for the amount (ml) titered of the 1/10 N $I_2$ solution, $f_1$ stands for the factor of the 1/10 N $Na_2S_2O_3$ solution, $f_2$ stands for the factor of the 1/10 N $I_2$ solution, S stands for the amount (g) of the lead monoxide sample, and the value of 0.03428 means the gram-equivalent of $PbO_n$ to 1 ml of the 1/10 N $I_2$ solution.

(F) Average Particle Size (Number Average)

By using an electron microscope (Super-Scope Model JEM-50 manufactured by Nippon Denshi K.K.), sizes of 200 to 300 particles sampled on a collodion-carbon vacuum-deposited film according to the water paste method were measured at a magnification of 1000 to 3000 to determine a number average particle size ($\mu$).

(G) True Density

A picnometer was filled with benzene and the weight (W) of benzene was measured. The temperature (Ti) was also measured by a thermometer equipped to the picnometer. Then, benzene was withdrawn from the picnometer, and a prescribed amount [M (g)] of a sample was charged into the picnometer and benzene was added. The picnometer was placed in a reduced pressure desiccator, and a reduced pressure of 3 mm Hg was maintained for 3 hours by using a vacuum pump. Then, the cock was closed and the vacuum pump was dismounted. Then, the picnometer was allowed to stand still at the temperature (Ti) overnight. The cock was opened and the picnometer was taken out. Benzene was added to fill the picnometer. The weight (W') and the temperature (Ti) were measured, and the density was calculated according to the following formula (11)

$$ds = \frac{M}{\frac{(M + W) - W'}{d}} \quad (11)$$

wherein ds denotes the density of the sample and d denotes the specific gravity of benzene at the temperature, Ti.

(H) Chromic Anhydride Reactivity

A 2-liter beaker was charged with 500 ml of water, and 69.06 g of the precisely weighed lead monoxide powder was put into water under mild agitation and sufficiently dispersed in water. Then, the temperature of the dispersion was elevated at 65° C. Then, 100 ml of an aqueous solution of chromic anhydride (30.94 g/100 ml of water) gradually added to the dispersion over a period of 30 minutes, and the mixture was aged at 65° C. for 60 minutes under agitation to thereby form crystals of lead chromate. The crystals of lead chromate were recovered by filtration through a filter paper No. 3, washed with water and dried at 110° C. The amount (g) of chromic anhydride ($CrO_3$) thus fixed as lead chromate was determined by the quantitative analysis. From the ratio of the thus determined amount (AC) (g) of chromic anhydride fixed as lead chromate to the amount (TC) (g) of chromic anhydride used, the chromic anhydride reactivity (RC) was calculated according to the formula (8) of $RC = (AT/TC) \times 100$.

(I) Measurement of Infrared Absorption Spectrum

The infrared absorption spectrum was automatically recorded in a wave length region of 4000 to 400 $cm^{-1}$ by using an infrared absorption spectrum measuring apparatus (Model IR-G manufactured by Nipon Bunko Kogyo K.K.) with respect to KBr tablets molded in vacuo ($3 \times 10^{-4}$ mm Hg) under a compression of 600 Kg/$cm^2$. The intensity of the absorption peak was evaluated according to the following scale:
vs: very strong
s: strong
m: mean
w: weak
b: broad
sh: shoulder

(J) Measurement of X-Ray Diffraction Pattern

The X-ray diffraction pattern was measured under the following conditions according to the powder method using an automatic recording X-ray diffraction apparatus (manufactured by Rigaku Kenki K.K.; X-ray generator = Cat. No. 2001; goniometer = Cat. No. 2227 for broad angle range measurement; counter = proportional counter):
target: Cu
filter: Ni
voltage: 30 KV
current: 15 mA
count range: 1000 cps
high pressure voltage: 1450 V
time constant: 1 sec
chart speed: 1 cm/min
scanning speed: 1°/min
diffraction angle: 17°–60.5°
slit width: 1°-1°-0.3

(K) Light Resistance

A sample (1 g) was placed on a glass sheet of an automatic Hoover muller and 0.6 ml of a vehicle (1:1 weight ratio mixture of castor oil and dioctyl phthalate) was added to the sample. The mixture was sufficiently kneaded by the muller to render it homogeneous. Then, the homogeneous mixture was placed to the glass sheet, and 3.7 g of a transparent clear lacquer was added and the mixture was sufficiently kneaded to form a homogeneous paste. The paste was coated in a uniform thickness on an art paper by using a film applicator having a clearance of 0.2032 mm and naturally dried to obtain a sheet for determination of the color difference.

The sheet was set at a position 36 cm distant from a high pressure mercury lamp for the fading test (Model H-400FT manufactured by Tokyo Shibaura Denki K.K.) and exposed to rays of the high pressure mercury lamp for 24 hours while the sheet was being rotated at 2 rpm.

The hues of the so irradiated sheet and the sheet which was not irradiated were measured by a color difference meter (Model ND-101D manufactured by Nippon Densyoku K.K.) and the color difference $\Delta E$ was determined from the following formula (12) according to the method of ASTM D1482-57T:

$$\Delta L = Lo - L$$
$$\Delta a = ao - a$$
$$\Delta b = bo - b$$
$$\Delta E = \sqrt{(\Delta L)^2 + (\Delta a)^2 + (\Delta b)^2} \quad (12)$$

Lo, ao, bo: hues before irradiation
L, a, b: hues after irradiation

(L) Content of Metallic Lead

According to the method of JIS K-1456 (determination of litharge), the amount of the acetic acid-insoluble component, namely metallic lead, was determined and expressed in terms of % by weight.

(M) Hue Stability 5 g of a sample was charged in an Ishikawa type automatic mortar and pulverized for 1 minute at a rotation number of 60 rpm, and the change of the hue by pulverization was examined and the hue stability was evaluated based on the change of the hue according to the following scale:

⊙: good hue stability without change of hue
Δ: slight change of hue
X: drastical change of hue (N) Hiding Power According to the method of JIS K-5104-1964 described above with respect to the measurement of the light resistance, a transparent clear lacquer-containing paste was prepared. The measurement was conducted by using a cryptometer and the hiding power was calculated according to the following formula (13):

$$HP \text{ (cm}^2\text{/g)} = \frac{W/d + V}{K \cdot L \times 0.1} \times \frac{1}{W} \quad (13)$$

in which W denotes the weight (g) of the sample, V denotes the amount (cc) of castor oil, d is a specific gravity of the sample, K is a constant of the cryptometer, and L denotes the distance (mm) at which the standard line becomes unseen.

TABLE 1

|  | Sample | | | | | |
| --- | --- | --- | --- | --- | --- | --- |
|  | A-1 | A-2 | A-3 | A-4 | A-5 | A-6 |
| Amount (Kg) of metallic lead granules | 200 | 200 | 200 | 50 | 200 | 200 |
| Amount (l) of liquid medium | 4 | 30 | 30 | 45 | 30 | 30 |
| Concentration (vol. %) of catalyst (HAc) | — | — | — | — | 0.2 | 0.1 |
| Rotation number (rpm) of mill | 60 | 60 | 120 | 120 | 50 | 50 |
| Reaction temperature (°C.) | 8 | 8 | 4 | 4 | 5 | 5 |
| Reaction time (min) | 30 | 30 | 30 | 30 | 30 | 30 |
| Oxygen pressure (Kg/cm$^2$) | 2 | 2 | 2 | 2 | 2 | 2 |
| Amount (g/hr) formed of PbO | 2227 | 2376 | 2340 | 415 | 3582 | 2793 |
| Oxygen absorption speed constant (Ka) | 0.452 | 0.473 | 0.466 | 0.165 | 0.713 | 0.556 |
| Conversion (%) to PbO | 2.07 | 1.10 | 2.17 | 0.77 | 1.66 | 1.30 |
| Selectivity (%) to PbO | 97.5 | 98.6 | 98.8 | 100 | 99.9 | 99.9 |
| Higher Lead Oxide ($-bO_n$) Content | 0.89 | 0.36 | 0.64 | 0.07 | 0.01 | 0.02 |
| Average particle size (μ) | 0.03 | 0.02 | 0.03 | 0.05 | 0.07 | 0.08 |
| Hue of recovered slurry | orange | orange | orange | white orange | pure white | white |
| True density (g/cc) | 9.18 | 9.18 | 9.14 | 9.01 | 8.38 | 8.42 |
| Chromic anhydride reactivity (RC, %) | 98.6 | 98.5 | 99.1 | 99.0 | 99.9 | 99.9 |
| Infrared absorption spectrum analysis 1400 cm$^{-1}$ | vs | vs | vs | vs | vs | vs |
| 840 cm$^{-1}$ | — | — | — | — | w | w |
| 680 cm$^{-1}$ | vs | vs | vs | vs | vs | vs |
| 490 cm$^{-1}$ | vs | vs | vs | vs | vs | vs |
| X-Ray diffraction pattern | M | M | L | L | H | H |
| Light resistance (ΔE) | 14 | 14 | 9 | 8 | 20 | 21 |
| Metallic lead content (%) | 0 | 0 | 0 | 0 | 0 | 0 |
| Hue stability | ⊙ | ⊙ | ⊙ | ⊙ | Δ | Δ |
| Hiding power (mm) | 100 | 105 | 140 | 120 | 130 | 155 |

EXAMPLE 1

In this Example, the process in which lead chromate is prepared by using the lead monoxide prepared in Referential Example according to the wet method as the starting material is described.

The massicot type lead monoxide of Sample A-2 (PbO$_n$ content=0.36%), the litharge type lead monoxide of Sample A-3 (PbO$_n$ content=0.64%) and the hydrate type lead monoxide of Sample A-5 (PbO$_n$ content=0.01%), each being prepared in Referential Example, were chosen as the starting lead monoxide powder. Water was added to the starting lead monoxide powder so that the PbO concentration in the resulting slurry was 140 g/l, and 493 ml of the PbO slurry was charged in a 2-liter capacity beaker. Hydroxylamine sulfate was added in an amount corresponding to 80% of the PbO$_n$ content (0.403 g in A-2, 0.717 g in A-3 or 0 g in A-5). Then, water was added so that the liquid volume was 500 ml. The dispersion was heated at 35° C. under sufficient agitation. Then, 100 ml of an aqueous solution of chromic anhydride (having a concentration of 30.94 g/100 ml) prepared separately was gradually added to the dispersion under agitation over a period of 180 minutes. Then, the mixture was agitated and aged for 60 minutes at a temperature maintained at 35° C. Thus, three kinds of crystals of lead chromate were prepared from the above three samples.

In 2 minutes from the start of addition of chromic anhydride, the pH value was changed from 9.9 to 7.3 and at the point of 3 minutes from the start of addition, the pH value was 5.8. At the point of 5 minutes from the start of addition, the pH value was 5.7. Then, the pH value was maintained at 2.7 to 3.2 while chromic anhydride was being added.

The so formed crystal of lead chromate was recovered by filtration using a filter paper No. 3, washed with water, dried at 110° C. and pulverized. Thus, three kinds of powdery lead chromate products (Samples 1-1, 1-2 and 1-3) were obtained.

With respect to each of the so prepared lead chromate products, the amount (g) of the starting chromic acid fixed as the lead chromate was determined by analysis, and from the ratio of the amount (AT) (g) of the fixed chromic acid to the amount (TC) (g) of the chromic acid used as the starting material, the chromic acid reaction ratio (RCR, %) was calculated according to the following formula (14) based on the above-mentioned formula (8):

$$RCR\ (\%) = \frac{AT}{TC} \times 100 \tag{14}$$

In order to know the properties of the so prepared lead chromate when used as the "chrome yellow" pigment, the hue, tinting power, light resistance and alkali resistance were checked according to the following methods. Obtained results are shown in Table 2.

(1) Tinting Power

In the same manner as described in the item "(J) Light Resistance" in the Referential Example, a sample (0.1 g) and 1.0 g of commercially available titanium oxide were placed on a glass sheet of an automatic Hoover Muller and 0.6 ml of a vehicle (1:1 weight ratio mixture of castor oil and dioctyl phthalate) was added to the sample. The mixture was sufficiently kneaded by the muller to render it homogeneous. Then, the homogeneous mixture was placed to the glass sheet, and 3.7 g of a transparent clear lacquer was added and the mixture was sufficiently kneaded to form a homogeneous paste. The paste was coated in a uniform thickness on an art paper by using a film applicator having a clearance of 0.2032 mm and naturally dried to obtain a sheet for determination of the tinting power. This sheet was compared with a comparative sheet of the original hue not tone-reduced by titanium oxide by the naked eye observation, and the tinting power was evaluated according to the following scale:

○: color strength comparable to that of the original hue not tone-reduced
Δ: ordinary
X: white hue similar to that of titanium dioxide (2) Light Resistance A sheet for determination of the color difference was prepared in the same manner as described in the item "(J) Resistance" in the Referential Example and was exposed to rays from a high pressure mercury lamp for the color fading test for 24 hours. The change of the hue was determined as the color difference ΔE by using a color difference meter. A smaller value of the color difference ΔE indicates a higher light resistance.

(3) Alkali Resistance

A sample (1 g) was charged in a 100-ml capacity test tube equipped with a common plug, and 80 ml of a 0.5% aqueous solution of Na)H was then charged in the tube and the tube was sealed. The tube was violently shaken for 30 minutes in a shaking machine. The solid was recovered by filtration and washed with water repeatedly to remove the alkali. The cake was dried at 100° C. for 2 hours and in the same manner as described in item "(J) Light Resistance" in the Referential Example, by using an automatic Hoover muller, a color paste was prepared from the dried cake and coated on an art paper by using a doctor knife to form a color sheet. The alkali resistance was evaluated based on the change of the hue, especially the degree of increase of redness by the alkali. Namely, when the degree of increase of redness was low and the change of the hue was small, it was evaluated that the alkali resistance was high.

For comparison, powdery lead chromate (Sample H-1) was prepared from commercially available conventional powdery lead monoxide (B-1) according to the conventional calcination method (litharge manufactured and sold by Mizusawa Kagaku Kogyo Kabushiki Kaisha, having a chromic anhydride reactivity, RC, of 74.0%) without using a catalyst in the same manner as described above, and the hue, tinting power, light resistance and alkali resistance of this product were tested according to the above-mentioned methods.

For another comparison, lead chromate (Sample H-2) was prepared from the above lead monoxide in the same manner as described above except that the reducing agent was not used.

The obtained results are shown in Table 2.

TABLE 2

| | Sample | | | | |
|---|---|---|---|---|---|
| | 1-1 | 1-2 | 1-3 | H-1 | H-2 |
| starting lead monoxide | A-2 | A-3 | A-5 | B-1 | A-3 |
| chromic acid reaction ratio (RCR) (%) | 97.9 | 98.5 | 99.9 | 73.5 | 98.5 |
| Hue | reddish yellow | reddish yellow | reddish yellow | blackish red-yellow | slightly blackish red |
| tinting power | | | | | |
| Light resistance (ΔE) | 17.9 | 18.3 | 19.1 | 42.3 | 18.5 |
| Alkali resistance | good | good | good | changed to red | good |

From the above results, it will readily be understood that even when the ultrafine particulate lead monoxide being excellent in the reactivity and light resistance but containing higher lead oxides is used as the starting lead monoxide according to this invention, if hydroxylamine sulfate is used as the reducing agent, lead chromate excellent in the hue and gloss can be prepared at a high chromic acid reaction ratio (RCR) by direct reaction with chromic anhydride without using a catalyst customarily used in the conventional process for the preparation of chrome yellow, such as nitric acid or acetic acid or without using sodium chromate or the like.

When conventional lead monoxide prepared by the calcination method is used as the starting lead monoxide, the amount of fixed chromic acid is very small and because of this small amount of fixed chromic acid, the hue of the resulting lead chromate is not good and the light resistance is low. In the conventional method, a catalyst such as acetic acid is used or sodium chromate is employed. Indeed, the amount of fixed chromic acid is increased and the hue is improved by such technique. However, in this case, chromium or sodium is transferred into the mother liquor separated from the lead chromate crystal or the washing liquor, and such mother liquor or washing liquor causes environmental pollution which is a serious social problem. A particular treatment is necessary for removal of the chromium and sodium components from the mother liquor or washing liquor, and various troubles are caused when lead chromate is prepared on an industrial scale according to such conventional method and those skilled in the art are harassed by these troubles actually occurring. In contrast, as will be apparent from the foregoing, occurrence of these troubles can completely be prevented according to this invention, and therefore, it will readily be understood that this invention will make great contributions to the art.

EXAMPLE 2

In this Example, the process for preparing lead compounds valuable as thermal stabilizers for vinyl chloride resins from the lead monoxide according to the wet method is illustrated.

The lead monoxide slurry Sample A-3 (having a PbO concentration of 78 g/l and containing 0.64% of $PbO_n$) prepared in the Referential Example was used as the starting lead monoxide, and powdery tribasic lead sulfate as a stabilizer for PVC resins was prepared according to the following procedures.

A 2-liter capacity beaker was charged with 1175.6 ml of the above lead monoxide slurry (containing 0.587 g of $PbO_n$ and having a pH value of 9.9) and 0.47 g of hydroxylamine sulfate was added (pH=9.6). Then, the temperature of the slurry was elevated under agitation by a glass vane. When the temperature was elevated to about 70° C., 26.22 ml of sulfuric acid having a concentration of 3.86 moles/l was promptly added to the slurry in about 10 seconds (the pH value was 6.2 at the initial stage of addition). The mixture was heated under agitation at 65° to 70° C. on a heater for 60 minutes to effect aging. Thus, a base slurry of tribasic lead sulfate (pH=8.3) was prepared.

Separately, a 200-ml capacity beaker was charged with 1.44 g of granular stearic acid, 2.08 ml of aqueous ammonia having a concentration of 0.736 mole/l and 50 ml of water, and the mixture was heated at 90° C. under violent agitation by a glass rod to completely emulsify stearic acid and form an ammonia soap. The so formed ammonia soap suspension was added to and sufficiently dispersed in the above-mentioned base slurry of tribasic lead sulfate, and the mixture was heated and aged at 65° to 70° C. for 60 minutes. The solid was recovered by filtration and the cake was dried overnight in a thermostat drier maintained at 90° C. and then pulverized by an atomizer to obtain a tribasic lead sulfate powder (Sample 2-1) having a very high whiteness.

Powdery tetrabasic lead sulfate for a stabilizer was prepared from the above-mentioned lead monoxide slurry according to procedures described below.

A 2-liter capacity beaker was charged with 1184.6 ml of the lead monoxide slurry A-3 (containing 0.591 g of $PbO_n$ and having a pH value of 9.9). Separately, 0.532 g of powdery hydroxylamine sulfate was dissolved in 50 ml of pure water under agitation, and the resulting solution was added to the above slurry. Then, slurry was heated on a plate heater under agitation by a glass vane. When the slurry temperature was elevated to 95° C., 0.70 ml of acetic acid having a concentration of 2.2 moles/l was added to the slurry and after agitation was conducted for 10 minutes, 26.84 ml of sulfuric acid having a concentration of 3.115 moles/l was gradually added dropwise to the slurry over a period of 30 minutes (the pH value was 6.8 at the initial stage of addition). After the dropwise addition, the liquid mixture was agitated and aged for 60 minutes while maintaining the liquid temperature at 93° to 97° C. to form a base slurry of tetrabasic lead sulfate having a pH value of 8.8.

Separately, a 200-ml capacity beaker was charged with 1.44 g of granular stearic acid, 2.36 ml of aqueous ammonia having a concentration of 0.648 mole/l and 50 ml of water, and the mixture was heated at 90° C. under agitation by a glass rod to completely emulsify stearic acid and form an ammonia soap.

The so prepared ammonia soap was added to and sufficiently dispersed in the above-mentioned base slurry of tetrabasic lead sulfate heated at 95° C., and the mixture was heated and aged at 93° to 97° C. for 60 minutes. After measurement of the pH (it was found that the pH was 8.7), the solid was recovered by filtration, and the cake was dried overnight in a thermostat drier maintained at 90° C. and pulverized by an atomizer to obtain a tetrabasic lead sulfate powder (Sample 2-2).

Powdery basic lead silicosulfate for a stabilizer was prepared from the above-mentioned lead monoxide slurry according to procedures described below.

The starting silicic acid component was formed in the following manner.

In a porcelain pot mill having a capacity of 1.7 liters, 48 g of commercially available finely divided silicic acid ("Mizukasil" manufactured by Mizusawa Kagaku Kogyo K. K.) was charged. Incidentally, 1.02 l of alumina balls having a diameter of 3 mm were contained in the porcelain ball mill. Then, 200 ml of water was poured into the ball mill, and wet pulverization was carried out for 24 hours at a rotation speed of 72 rpm. The resulting slurry was used as the starting silicic acid component.

About 200 ml of the so formed slurry as transferred into a beaker having a capacity of 2 liters, and 615.6 ml of the above-mentioned novel lead monoxide slurry A-3 (having a PbO concentration of 78 g/l and containing 0.307 g of $PbO_n$) was added thereto under agitation to form a homogeneous mixed slurry of silicic acid and lead monoxide (pH=8.9). Then, 0.24 g of powdery hydroxylamine sulfate was added to the slurry (pH=8.7) and 8.5 ml of sulfuric acid having a concentration of 5.375 moles/l was gradually added to the mixed slurry (the pH value was 5.7 at the initial stage of addition) and the mixture was agitated and aged for 2 hours at room temperature. Then, the temperature was elevated and the slurry was maintained at 70° C. to effect aging and formation of crystals of basic lead silicosulfate (the pH value of the slurry was 7.8).

Separately, 7.67 g of lauric acid and 19.4 ml of the above-mentioned lead monoxide slurry were charged in a beaker having a capacity of 200 ml, and 50 ml of water was added thereto. Then, the temperature was elevated to 65° C. and the mixture was violently agitated by a glass rod to form a lauric acid soap suspension.

The so formed soap suspension was gradually added to the above-mentioned slurry of basic lead silicosulfate maintained at 70° C. and the mixture was agitated and aged for 60 minutes. The solid was recovered by filtration, dried at 65° C. for 7 hours and pulverized to obtain a basic lead silicosulfate powder (Sample 2-3).

Dibasic lead phosphite for a stabilizer was prepared from the above-mentioned lead monoxide slurry according to procedures described below.

A 2-liter capacity beaker was charged with 1136.2 ml of the lead monoxide slurry A-3 (containing 0.567 g of $PbO_n$) and 0.51 g of powdery hydroxylamine sulfate was added (the slurry pH value was 9.4). Then, the slurry was heated at 65°±5° C. on a heater under agitation by a glass vane. Then, 0.30 ml of acetic acid having a concentration of 2.713 mole/l was added dropwise to the slurry and sufficiently dispersed in the slurry. Then, 37.91 ml of phosphorous acid ($H_2HPO_3$) having a concentration of 3.448 moles/l was added dropwise to the slurry over a period of 30 minutes (the pH value was 6.3 at the initial stage of addition) and aging was conducted under heating and agitation for 60 minutes to form a dibasic lead phosphite slurry having a pH value of 7.8.

Separately, 100 ml of pure water was charged in a 200-ml capacity beaker and heated at 80° C., and 0.93 g of stearic acid was added to heated water under agitation by a glass rod to melt stearic acid. Then, 0.21 ml of aqueous ammonia having a concentration of 3.953 moles/l was added to the mixture under violent agitation to completely emulsify stearic acid and form an ammonia soap suspension having a pH value of 10.5.

The so formed suspension was poured to the above-mentioned warm slurry of dibasic lead phosphite over a period of 10 minutes, and the mixture was heated and aged under agitation for 30 minutes (it was found that the pH was 7.5). The solid was separated by filtration, dried overnight in a thermostat drier maintained at 60° C. and pulverized in a mortar to obtain a dibasic lead phosphite powder (Sample 2-4).

Lead phthalate for a stabilizer was prepared from the above-mentioned lead monoxide slurry according to procedures described below.

The lead monoxide slurry A-3 prepared in the Referential Example was dried at low temperatures, and water was added to the resulting powder to form a slurry having a concentration of 140 g/l and a pH value of 9.8.

A 2-liter beaker was charged with 563 ml of the so formed slurry (containing 0.504 g of $PbO_n$) and 0.45 g of powdery hydroxylamine sulfate was added to the slurry (the pH value was 9.5). Then, the slurry was heated on a heater at 65°±5° C. under agitation by a glass vane. Then, 29.81 ml of acetic acid having a concentration of 7.781 moles/l was added dropwise to the slurry over a period of 15 minutes to form a liquid mixture [I] having a pH value of 4.9.

Separately, a 300-ml capacity beaker was charged with 200 ml of water and 17.09 g of phthalic anhydride, and the mixture was heated at 70°–80° C. by a heater and 40.55 ml of an aqueous solution of sodium hydroxide (NaOH) having a concentration of 5.692 moles/l was added dropwise to the mixture under agitation by a glass vane to form a sodium phthalate solution [II] having a pH value of 12.2.

Separately, in a 200-ml capacity beaker, 1.32 g of granular stearic acid was added to 100 ml of water, and the mixture was heated at 80° C. on a heater under agitation by a glass rod to melt stearic acid. Then, 0.55 ml of aqueous ammonia having a concentration of 2.102 moles/l was added and the mixture was violently agitated to completely emulsify stearic acid and form an ammonia stearate soap suspension [III].

Then, the solution [II] was added dropwise to the liquid mixture [I] heated at 65°±5° C. over a period of 30 minutes, and the mixture was aged under heating and agitation for 60 minutes and the suspension [III] was added thereto dropwise over a period of 10 minutes. The mixture was further aged for 30 minutes. Then, the pH was measured (it was found that the pH was 10.5), and the solid was recovered by filtration, dried overnight in a thermostat drier maintained at 105° C. and pulverized by an atomizer to obtain a lead phthalate powder (Sample 2-5).

Dibasic lead stearate for a stabilizer was prepared from the above-mentioned lead monoxide slurry according to procedures described below.

A 2-liter capacity beaker was charged with 392 ml of the above-mentioned lead monoxide slurry (having a pH value of 9.8 and a PbO concentration of 140 g/l and containing 0.351 g of $PbO_n$) and 0.28 g of hydroxylamine hydrochloride was added (pH=9.6). Then, the slurry was heated at 65° C. on a heater under agitation by a glass vane. Then, 27.67 ml of acetic acid having a concentration of 1.481 moles/l was added to the slurry to form a lead monoxide dispersion.

Separately, 46.57 g of granular stearic acid was added to 1.5 l of pure water charged in a 2-liter capacity beaker, and the mixture was heated at 75° C. on a heater under agitation by a glass vane to melt stearic acid. Then, 44.81 ml of aqueous ammonia having a concentration of 0.9145 mole/l was added to completely emulsify stearic acid and form an ammonia soap suspension.

The so formed ammonia soap suspension was added dropwise to the above-mentioned lead monoxide dispersion over a period of 35 minutes under agitation to effect reaction. The mixture was heated and aged under agitation for 60 minutes to form dibasic lead stearate. At this point, the pH of the reaction mixture was 7.58. The solid was recovered by filtration, dried overnight in a thermostat drier maintained at 60° C. and pulverized by an atomizer to obtain a dibasic lead stearate powder (Sample 2-6).

Lead stearate was prepared from lead monoxide powder formed by drying at low temperatures the lead monoxide slurry (Sample A-6 containing 0.01% of $PbO_n$) obtained in the Referential Example according to the melting method by procedures described below.

A 500-ml capacity beaker was charged with 147 g of stearic acid and it was molten at 160°±5° C. in an oil bath under agitation by a glass vane, and 57.74 g of the lead monoxide powder (Sample A-6) and 0.31 g of powdery hydroxylamine sulfate were gradually added to the melt to effect reaction. Then, aging was conducted for 15 minutes to obtain a melt of lead stearate. The melt was poured into a watch glass and naturally cooled. The resulting solid was pulverized by an atomizer to obtain a lead stearate powder (Sample 2-7).

Tribasic lead sulfates were prepared from the two kinds of lead monoxide powders obtained by drying at low temperatures the lead monoxide slurrys (Samples A-1 and A-4) obtained in the Referential Example according to procedures described below.

Water was added to the starting lead monoxide powder containing 0.89% or 0.07% of $PbO_n$ to form a slurry having a PbO concentration of 93 g/l and a pH value of 9.8. A 2-liter capacity beaker was charged with 985 ml of the so prepared lead monoxide slurry, and 0.7 ml of acetic acid having a concentration of 2.2 moles/l was added to the slurry on a water bath under agitation by a glass vane. The mixture was agitated for 10 minutes, and 0.8 ml of hydroxylamine sulfate having a concentration of 0.84 mole/l and 0.03 g of powdery tartaric acid were added to the mixture. The mixture was sufficiently agitated to reduce lead peroxide present in the lead monoxide slurry (pH=9.7), and then, the mixture was heated. When the slurry temperature was elevated to 65° to 70° C., 26.61 ml of sulfuric acid having a concentration of 3.861 moles/l was gradually added dropwise to the slurry over a period of 30 minutes (the pH value was 6.3 or 6.4 at the initial stage of addition) and the mixture was agitated at 65° to 70° C. for 40 minutes to effect aging. Thus, there were obtained two kinds of tribasic lead sulfate base slurries having pH values of 8.4 and 8.5, respectively.

Separately, a 200-ml capacity beaker was charged with 1.44 g of granular acetic acid, 2.08 ml of aqueous ammonia having a concentration of 0.736 mole/l and 50 ml of water, and the mixture was heated at 90° C. under agitation on by a glass rod to completely emulsify stearic acid and form an ammonia soap suspension.

The so formed ammonia soap suspension was poured and dispersed in the above tribasic lead sulfate base slurry, and the mixture was heated and aged at 65° to 70° C. for 60 minutes. The pH was measured (it was found that the pH was 7.5 or 7.6), and the solid was recovered by filtration, dried overnight in a thermostat drier maintained at 90° C. and pulverized by an atomizer. Thus, two kinds of tribasic lead sulfate powders (Samples 2-8 and 2-9) were obtained.

In order to know effects of the so prepared 9 lead compounds as stabilizers of vinyl chloride resins, they were subjected to the following tests to obtain results shown in Table 3.

Stabilizer Test Methods (1) Thermal Stability (Hydrogen Chloride-Catching Property)

50 Parts by weight of dioctyl phthalate (manufactured by Kyowa Hakko K. K.) was added to 100 parts by weight of a vinyl chloride resin (VINYCLON 4000M manufactured by Mitsui Toatu), and 5 parts by weight of a sample was added to the mixture. The mixture was sufficiently blended, kneaded at 155° C. for 10 minutes by means of a kneading roll having a diameter of 3.5 inches, and taken out in the form of a sheet having a thickness of about 0.5 mm. Three of the so formed sheets were piled and pressed at 170° C. under a pressure of 200 Kg/cm² for 10 minutes to obtain a sheet having a thickness of about 1 mm. Then, the sheet was cut into pieces having a volume of about 0.5 mm³, and 2 g of the so formed pieces were charged in a test tube having a diameter of 1.5 cm. A Congoo Red test paper wetted with glycerin was fixed to the mouth of the test tube so that it did not touch the wall of the test tube. The test tube was dipped in an oil bath maintained at 180° C. and the time required for bluing of the Congoo Red test paper by hydrogen chloride formed as a result of the thermal decomposition of the vinyl chloride resin was measured. The heat stability (chlorine-catching property) was evaluated based on the above time (minutes). The longer the time (minutes) required for bluing, the higher the stabilizing effect against thermal decomposition.

(2) Light Resistance

A press sheet of the lead compound stabilizer-incorporated vinyl chloride resin, prepared according to the same method as described in (1) above, was exposed to rays from a high pressure mercury lamp for the color fading test for 3 hours in the same manner as described in the item "(J) Light Resistance" in the Referential Example. The change of the hue (color difference ΔE) was determined by a color difference meter, and the light resistance was evaluated based on the so determined color difference. Namely, a smaller value of the color difference ΔE indicates a higher light resistance.

(3) Electric Insulating Property (Volume Resistivity)

A press sheet of the lead compound stabilizer-incorporated vinyl chloride resin, prepared according to the same method as described in (1) above, was tested according to the method of JIS K-6723, Paragraphs 7 and 8 to determine the volume resistivity (Ω-cm).

More specifically, the press sheet was allowed to stand under constant conditions in a desiccator for at least 24 hours. Then, the sample sheet was maintained at a constant temperature of 30±2° C. in a thermostat tank and the volume resistivity (Ω-cm) of the sample sheet was measured by an ultrasuper insulating-resistance meter (Model SM-10 manufactured by Toa Denpa Kogyo K. K.). The volume resistivity was determined after correction of the thickness and the like.

(4) Dispersibility

In order to know the dispersibility of the stabilizer, the following test was carried out.

0.05 part by weight of carbon black (Seast H manufactured by Tokai Denkyoku K. K.) was homogeneously incorporated into 100 parts by weight of a commercially available vinyl chloride resin (Sumilite SX-11F manufactured by Sumitomo Kagaku Kogyo K. K.), and 2.0 g of the mixture was weighed by a balance (sensitivity of 0.1 g) and charged into a 100-ml capacity beaker. Then, 12 g of dioctyl phthalate (manufactured by Kyowa Hakko K. K.) was charged into the beaker and 1 g of a sample was added. The contents of the beaker was let to fall down on a double-roll kneader having a diameter of 3.5 inches and maintained at a surface temperature of 160° C. (the friction ratio being 1.25) without substantial blending of the contents, and the kneading was conducted for 10 minutes and the kneaded mixture was taken out in the form of a sheet having a thickness of 0.2 mm. When the sample added was not sufficiently dispersed, there were observed white spots on the surface of the resulting black sheet. Accordingly, the numbers of small white spots having a size of 0.1 to 0.2 mm, medium small spots having a size of 0.2 to 0.3 mm and white spots having a size larger than 0.3 mm, which appeared in a square region of 100 mm × 10 mm on the black sheet, were counted, and the dispersibility was evaluated based on the number of white spots. Namely, when the number of white spots was larger, the dispersibility was evaluated as worse and when white spots were not observed, the dispersibility was evaluated as good.

In order to clarify the effects of this invention, the following comparative experiment was carried out.

By using conventional lead monoxide powder according to the calcination method (litharge manufactured and sold by Mizusawa Kagaku Kogyo K.K.), which was used as the comparative lead monoxide in Example 1, it was tried to prepare a tribasic lead sulfate powder (Sample H-2) without using acetic acid as a catalyst under the same conditions as adopted above for the production of Sample 2-1.

For another comparison, tribasic lead sulfate was prepared from the lead monoxide slurry A-3 (having a PbO concentration of 78 g/l and containing 0.64% of $PbO_n$) without using a reducing agent such as hydroxylamine sulfate according to the following procedures.

A 2-liter beaker was charged with 1175.6 ml of the lead monoxide slurry A-3 (containing 0.587 g of $PbO_n$) and the slurry was heated under agitation with a glass vane, and when the temperature was elevated to about 70° C., 26.22 ml of sulfuric acid having a concentration of 3.86 mole/l was promptly added to the slurry in about 10 seconds (the pH value was 6.2 at the initial stage of addition). The temperature was maintained at 65° to 70° C. while heating the slurry on a heater under agitation, and in this state, aging was carried out for 60 minutes to obtain a base slurry of tribasic lead sulfate.

Separately, a 200-ml beaker was charged with 1.44 g of granular stearic acid, 2.08 ml of aqueous ammonia having a concentration of 0.736 mole/l and 50 ml of water, and the mixture was heated at 90° C. under violent agitation with a glass rod to effect complete emulsification and prepare an aqueous ammonia soap. The so formed soap was added to the above base slurry of tribasic lead sulfate and the resulting dispersion was heated and aged at 65° to 70° C. for 60 minutes. The resulting mixture was filtered and the cake was dried overnight in a thermostat drier maintained at 90° C. The dried cake was pulverized by an atomizer to form powdery tribasic lead sulfate (Sample H-4).

For still another comparison, tribasic lead sulfate was prepared from the lead monoxide slurry A-3 (having a PbO concentration of 78 g/l and a pH value of 9.9 and containing 0.64% of $PbO_n$) by using tartaric acid as a reducing agent according to the following procedures.

A 2-liter beaker was charged with 1175.6 ml of the lead monoxide slurry A-3 (containing 0.587 g of $PbO_n$) and 0.7 g of powdery tartaric acid was added to the slurry under agitation with a glass vane (pH=9.7). The mixture was heated and when the temperature was elevated to about 70° C., 26.22 ml of sulfuric acid having a concentration of 3.86 mole/l was promptly added to the slurry in about 10 seconds (the pH value was 5.7 at the initial stage of addition). The temperature was maintained at 65° to 70° C. while heating the slurry on a heater under agitation, and in this state, aging was carried out for 60 minutes to obtain a base slurry of tribasic lead sulfate having a pH value of 8.4.

Separately, a 200-ml beaker was charged with 1.44 g of flaky stearic acid, 2.08 ml of aqueous ammonia having a concentration of 0.736 mole/l and 50 ml of water, and the mixture was heated at 90° C. under violent agitation with a glass rod to effect complete emulsification and prepare an aqueous ammonia soap. The so formed soap was added to the above base slurry of tribasic lead sulfate and the resulting dispersion was heated and aged at 65° to 70° C. for 60 minutes (pH=8.4). The resulting mixture was filtered and the cake was dried overnight in a thermostat drier maintained at 90° C. The dried cake was pulverized by an atomizer to form powdery tribasic lead sulfate (Sample H-5).

Similarly, tribasic lead sulfate powder (Sample H-6) was prepared by using hydrazine sulfate as a reducing agent instead of tartaric acid.

It was found that when the commercially available litharge was used, because of a poor reactivity of the starting litharge, it was impossible to obtain a tribasic lead sulfate stabilizer excellent in the hue and other properties without using a catalyst such as acetic acid or promoting the reaction by particular means.

It was also found that hydroxylamine sulfate, hydroxylamine hydrochloride and a combination of hydroxylamine sulfate and tartaric acid are effective as the reducing agent, and when tartaric acid or hydrazine sulfate is used singly, the reducing activity is low.

When the above conventional lead monoxide powder according to the calcination method was used as the starting lead monoxide and tribasic lead sulfate was prepared in the same manner as described above, in order to obtain a product comparable to a white powdery stabilizer of the above-mentioned tribasic lead sulfate (Sample 2-1) prepared from the novel lead monoxide without using a catalyst such as acetic acid, it was necessary to use 2.5 ml of acetic acid having concentration of 2.2 moles/l under the above-mentioned preparation conditions. Further, in this case, the dissolved lead component was contained in the mother liquor left after recovery of the formed tribasic lead sulfate at a concentration of about 1.5 g/l. Therefore, it was found that if this mother liquor is discharged as it is, a social problem of environmental pollution will inevitably be caused. In contrast, when the novel ultrafine particulate lead monoxide having a high reactivity is used as a starting material for production of a stabilizer according to this invention, a social problem such as environmental pollution is not caused because the lead component or acetic acid or the like catalyst is not contained in waste water in the dissolved state, and a lead compound stabilizer can be conveniently prepared according to this invention.

In order to compare the lead compound stabilizers prepared in this Example with commercially available lead compound stabilizers, stabilizers shown in Table 4 were chosen among commercially available stabilizers of the "Stabinex" series (product of Mizusawa Kagaku Kogyo K.K.) and they were subjected to the above-mentioned tests to obtain results shown in Table 4.

TABLE 3

| Lead Compound | Sample | Hue of Sheet | Light Resistance (ΔE) | Thermal Stability (minutes) | Insulating Property (× $10^{13}$ Ω-cm) |
|---|---|---|---|---|---|
| tribasic lead sulfate | 2-1 | white | 16.3 | 410 | 4.9 |
| tetrabasic lead sulfate | 2-2 | lightly yellowish white | 13.1 | 450 | 6.8 |
| basic lead silicosulfate | 2-3 | white | 21.0 | 184 | 1.1 |
| dibasic lead phosphite | 2-4 | white | 18.4 | 84 | 7.0 |
| lead phthalate | 2-5 | lightly yellowish white | 18.3 | 31 | 1.7 |
| dibasic lead stearate | 2-6 | lightly yellowish white | 20.1 | 230 | 0.9 |
| lead stearate | 2-7 | white and transparent | 12.4 | 39 | — |
| tribasic lead sulfate | 2-8 | white | 14.4 | 420 | 5.3 |
| tribasic lead sulfate | 2-9 | pure white | 19.1 | 378 | 5.2 |
| tribasic lead sulfate | H-3 | lightly browish white | 27.4 | 390 | 4.7 |
| tribasic lead sulfate | H-4 | yellowish brown | 15.0 | 400 | 5.0 |
| tribasic lead sulfate | H-5 | lightly violet white | 28.2 | 322 | 5.1 |
| tribasic lead sulfate | H-6 | yellowish brown | 28.4 | 376 | 4.3 |

TABLE 4

| Lead Compound | Hue of Sheet | Light Resistance | Thermal Stability | Insulating Property ($\times 10^{13}$ Ω-cm) |
|---|---|---|---|---|
| tribasic lead sulfate | white | 29.2 | 365 | 1.8 |
| tetrabasic lead sulfate | lightly yellowish white | 26.2 | 312 | 5.5 |
| basic lead silicosulfate | white | 34.5 | 122 | 0.7 |
| tribasic lead phosphite | white | 36.2 | 67 | 5.5 |
| lead phthalate | lightly yellowish white | 33.2 | 240 | 0.8 |
| dibasic lead stearate | lightly yellowish white | 34.2 | 203 | 0.7 |
| lead stearate | white and transparent | 19.3 | 35 | — |
| tribasic lead sulfate | white | 27.4 | 370 | 4.7 |

EXAMPLE 3

A process for preparing lead compounds for pigments from the lead monoxide according to the wet method is described in this Example.

The lead monoxide slurry of Sample A-2 prepared in the Referential Example (containing 0.36% of $PbO_n$) was dried at low temperatures and the resulting ultra-fine particulate lead monoxide was used as the starting lead monoxide, and it was diluted with water to form a slurry having a PbO concentration of 80 g/l (containing 0.288 g/l of $PbO_n$).

Preparation of lead cyanamide, which is broadly used as an anti-corrosive agent, was tried by using the so prepared lead monoxide slurry.

A cyanamide solution obtained by treating lime nitrogen (a product of Shinetsu Kagaku Kogyo K.K. containing 50% of calcium cyanamide) according to the following method was used as the starting cyanamide.

A 10-liter capacity stainless steel beaker was charged with 1 Kg of the above-mentioned lime nitrogen and 4 l of cold water. The leaching treatment was conducted for about 30 minutes under violent agitation. Since the temperature of the liquid was gradually elevated by the reaction heat, the liquid temperature was controlled to 30° to 35° C. by cooling.

Insoluble substances such as calcium hydroxide were removed by filtration using a Buchner funnel to obtain a transparent solution of acidic calcium cyanamide. Carbon dioxide gas was promptly blown into this solution at room temperature to effect neutralization until the pH was 6.5 to 7.0 (about 120 minutes were necessary). The formed calcium carbonate precipitate was removed by filtration to obtain about 3.6 l of a filtrate having a cyanamide concentration of 4.77 g/100 ml. The yield was about 68.7%.

A 5-liter capacity beaker was charged with 1142 ml of the above-mentioned lead monoxide slurry (containing 0.329 g of $PbO_n$ and having a pH value of 9.8). Then, 3000 ml of pure water was added and the mixture was gently agitated at room temperature (20° to 25° C.), and 0.26 g of hydroxylamine hydrochloride was added to 357 ml of the cyanamide solution (having a concentration of 4.77 g/100 ml) prepared according to the above-mentioned method and the mixture (pH=7.4) was added dropwise to the above slurry over a period of 20 minutes to effect reaction. The pH was adjusted to 10 by using 2 to 3 ml of 15 N aqueous ammonia, and the reaction mixture was aged under agitation for 120 minutes at 20° to 25° C. The solid was recovered by filtration and dried below 80° C. to obtain 105 g of lead cyanamide. The product was pulverized to obtain a lead cyanamide powder (Sample 3-1).

Pigment characteristics of the so prepared lead cyanamide were tested according to the following methods to obtain results shown in Table 5.

Methods of Tests of Pigment Characteristics (1) Density

The density was determined according to the customary method using a pycnometer and benzene as a medium.

(2) Water-Insoluble Component Content

The water-insoluble component content was determined according to the pigment test method of JIS K-5101. Namely, 2 g, precisely weighed, of a sample was charged in a 500-ml capacity beaker, and 200 ml of distilled water was added. The mixture was boiled for 5 minutes and naturally cooled to room temperature. Then, the mixture was transferred to a graduated flask having a capacity of 250 ml and water was added so that the liquid level reached an indicator line of 250 ml. The mixture was sufficiently shaken and filtered by using a filter paper No. 5C. First 50 ml of the filtrate was thrown away, and 100 ml of the subsequent filtrate was sampled on an evaporating dish having a known weight and subjected to evaporation to dryness. The solid was then dried for 2 hours and naturally cooled in a desiccator. The water-insoluble component was calculated according to the following formula (14):

$$M = \frac{2.5N}{S} \times 100 \quad (14)$$

in which M represents the water-insoluble component content (%), N stands for the amount (g) of the evaporation residue, and S stands for the weight (g) of the sample.

(3) Oil Absorption

A sample (5 g) was placed on a glass sheet, and boiled linseed oil was dropped little by little to the center of the sample. Every time the linseed oil was dropped, the entire mixture was sufficiently kneaded by a steel spatula. The dropping and kneading operations were repeated until the entire mixture became one solid putty-like mass which could be peeled from the glass sheet in the spiral form wound on the spatula. The oil absorption was calculated according to the following formula (15):

$$G = \frac{H}{S} \times 100 \quad (15)$$

in which G stands for the oil absorption (%), H represents the amount (ml) of boiled linseed oil dropped and S designates the weight (g) of the sample.

(4) Specific Resistance and pH

A 200-ml capacity beaker was charged with 10 g, precisely weighed, of a sample, and 100 ml of distilled water was added thereto. The mixture was agitated for 5 minutes by a magnet stirrer, and was then allowed to stand at room temperature for 3 hours. Then, the mixture was filtered by a filter paper No. 3 under agitation by a glass rod. The specific resistance of the filtrate was measured by a conductivity measuring cell (Model CM-6A manufactured by Toa Denpa K.K.) and the pH of the filtrate was measured by a pH meter (Model HM-6A manufactured by Toa Denpa K.K.).

(5) Hue

The sample powder was examined with the naked eye to determine the hue.

(6) Anti-Corrosive Effect

An anti-corrosive paint was prepared according to the following method.

By using a 6-cylinder type sand grinder (manufactured by Igarashi Kikai Seizo K.K.), in a 500-ml capacity stainless steel vessel filled with 200 g of glass beads having a diameter of 1 mm, components described below were blended for 10 minutes at a grinder rotation speed of 1860 rpm, and the supernatant paint (300 ml) was transferred into a can.

| Composition of Paint: | |
|---|---|
| Alkyd resin (P-470-70 manufactured by Dainippon Ink K.K.) | 140 g |
| Calcium carbonate (extender pigment) | 40 g |
| Lead cyanamide (anti-corrosive paint) | 8 g |
| Thinner (1500 manufactured by Nippon Paint K.K.) | 20 ml |

A steel plate having a size of 1.0 mm × 70 mm × 150 mm (manufactured by Nippon Test Panel Kogyo K.K.) was subjected to wet grinding using an abrasive paper No. 500 and was then dried and degreased by a thinner. Then, the above paint was brush-coated on the steel plate and the coated plate was dried overnight at room temperature. Then, the paint was coated again and the coated plate was dried overnight at room temperature to obtain a test plate.

The test plate was tested according to the water resistance and salt spray test methods described in JIS K-5400, 7.2 and 7.8, and the change of the coated surface was examined after the lapse of 7 or 14 days and the anti-corrosive effect was evaluated according to the following scale:
A: no rust noted.
B: rusts noted on a slight number of pinholes.
C: rusting of parts of the test plate, and cracks and bulges of parts of the film coating.
D: a major part of the test plate rusted, and a major part of the film coating peeled off.
E: rupture of the film coating and rusting over the whole of the substrate.

For comparison, lead cyanamide (Sample H-7) was prepared in the same manner as described above by using the same conventional powdery lead monoxide according to the calcination method (litharge manufactured by Mizusawa Kagaku Kogyo K.K.) as used in Example 1.

Since the unreacted PbO component was left in the so prepared comparative lead cyanamide, the product had a reddish brown or reddish yellow color of a low chroma. Namely, it was found that under the above-mentioned conditions adopted for production of lead cyanamide by direct reaction of the novel ultrafine particulate lead monoxide with the cyanamide component, no lead cyanamide having good properties can be prepared from the conventional lead monoxide according to the calcination method. In order to obtain a product comparable to the above-mentioned lead cyanamide according to this invention, it was necessary to adopt the conventional technique of double decomposition between lead nitrate and calcium cyanamide. In this case, however, formation of calcium nitrate as a by-product to be discarded could not be avoided. The lead cyanamide (Sample H-7) prepared by using the conventional lead monoxide (litharge) formed according to the calcination method was subjected to the above-mentioned tests of pigment characteristics to obtain results shown in Table 5.

TABLE 5

| | Sample | |
|---|---|---|
| | 3-1 | H-7 |
| Density (g/cc) | 6.44 | 6.67 |
| Water-insoluble component content (%) | 0.45 | 1.14 |
| Oil absorption (cc/100 g) | 9.69 | 11.6 |
| Specific resistance (K Ω-cm) | 52.6 | 12.4 |
| pH | 8.2 | 9.5 |
| Hue | clear yellow | red-brown yellow |
| Anti-corrosive effect | | |
| water resistance test (14 days) | B | B |
| salt spray test (7 days) | B | C |

What is claimed is:
1. A process for the preparation of water insoluble lead compounds having a composition represented by the following general formula

$nPbO \cdot PbX_{2/x}$ wherein X stands for an inorganic acid or organic acid radical, x indicates the valency of the radical X and n is a number of from 0 to 5, which comprises reacting a lead monoxide with an acidic component which is a corresponding inorganic acid, its acidic oxide, a corresponding organic acid or an acid anhydride of said organic acid of an acetic acid or of an acetic acid or in the presence of no more than a catalytic amount of an acetic acid, wherein the lead monoxide is a lead monoxide containing a higher lead oxide selected from the group consisting of lead dioxide and minimum in an amount of 0.001 to 5% by weight based on the total weight and being obtained by charging granules of metallic lead, an aqueous liquid medium and oxygen in a rotary mill, rotating the rotary mill under such conditions that at least parts of the metallic lead granules wetted with the liquid medium are located in the gas phase above the level of the liquid medium and friction is caused among the metallic granules through the liquid medium, to thereby form a dispersion of very fine particles of lead monoxide in the liquid medium and separating the dispersion from the metallic lead granules, and wherein the lead monoxide in the form of the as-prepared dispersion is mixed with said acidic component in the presence of 0.001 to 5% by weight, based on the lead monoxide, of an acid addition salt of hydroxylamine with a nonoxidizing acid under such conditions that the initial pH value of the mixture is maintained at a level not higher than 7, said acid addition salt being present in an amount sufficient to reduce most or all the lead dioxide or minimum in the starting lead monoxide.

2. The process of claim 1 wherein the acid addition salt of hydroxylamine is hydroxylamine sulfate or hydroxylamine hydrochloride.

3. The process of claim 1 or claim 2 wherein the acid addition salt of hydroxylamine is present in an amount of 0.01 to 2% by weight, based on the lead monoxide and the initial pH value of the mixture is maintained at a level not higher than 6.5.

4. The process of claim 1 wherein said acidic component is a corresponding inorganic acid selected from the group consisting of sulfuric acid, sulfurous acid, phosphoric acid, phosphorus acid, carbonic acid, chromic acid, molybdic acid, tungstic acid and silicic acid or an acidic oxide of any of these acids.

5. The method of claim 1 wherein said acidic component is a corresponding organic acid selected from the group consisting of phthalic acid, isophthalic acid, terephthalic acid, benzoic acid, salicylic acid, p-hydroxybenzoic acid, naphthoic acid, naphthalene-dicarboxylic acid, biphenyl-dicarboxylic acid, maleic acid, fumaric acid, itaconic acid, 2-ethylhexanoic acid, palmitic acid, stearic acid, oleic acid, linoleic acid, oxo-process branched fatty acids, Koch-process neo-acids, naphthenic acid, hexahydroterephthalic acid, tetrahydrophthalic acid and cyanamide or an acid anhydride of any of these organic acids.

6. The method of claim 1 which is carried out in the absence of acetic acid.

7. The process of claim 1 which is carried out in the presence of a catalytic amount of acetic acid.

8. The process of claim 1 or claim 2 wherein the lead monoxide in the form of the as-prepared dispersion is mixed with said acidic component and the acid addition salt of hydroxylamine in the further presence of from about 0.05 to 10% by weight, based on the lead monoxide of a reducing assistant selected from the group consisting of tartaric acid, citric acid, gallic acid, glucose, ascorbic acid, sucrose, urea and urea derivatives.

* * * * *

UNITED STATES PATENT AND TRADEMARK OFFICE
CERTIFICATE OF CORRECTION

PATENT NO. : 4,324,768
DATED : April 13, 1982
INVENTOR(S) : SUGAHARA, ET AL.

It is certified that error appears in the above—identified patent and that said Letters Patent is hereby corrected as shown below:

On the title page

Assignee: Mizusawa Kagaku Kogyo Kabushiki Kaisha, Osaka, Japan

Column 38, line 53, delete "of an acetic acid or of an acetic acid or".

Signed and Sealed this

Third Day of August 1982

[SEAL]

Attest:

GERALD J. MOSSINGHOFF

Attesting Officer

Commissioner of Patents and Trademarks